(12) United States Patent
Mills et al.

(10) Patent No.: US 7,648,676 B2
(45) Date of Patent: Jan. 19, 2010

(54) PROCESS AND APPARATUS FOR TREATING IMPLANTS COMPRISING SOFT TISSUE

(75) Inventors: C. Randal Mills, Baltimore, MD (US);
John R. Bianchi, Blacksberg, TN (US);
Michael R. Roberts, Bel Air, MD (US);
Chandrasekaran Nataraj, Alachua, FL (US)

(73) Assignee: RTI Biologics, Inc., Alachua, FL (US)

( * ) Notice: Subject to any disclaimer, the term of this patent is extended or adjusted under 35 U.S.C. 154(b) by 314 days.

(21) Appl. No.: 10/828,653

(22) Filed: Apr. 20, 2004

(65) Prior Publication Data
US 2005/0229323 A1    Oct. 20, 2005

(51) Int. Cl.
*A61L 2/00* (2006.01)
*A61L 2/18* (2006.01)
*A61L 9/00* (2006.01)
*B01D 11/02* (2006.01)
*B01D 12/00* (2006.01)
*B01D 15/00* (2006.01)
*B08B 3/00* (2006.01)

(52) U.S. Cl. ............... 422/28; 422/261; 422/292; 422/300; 134/26; 134/34; 134/36

(58) Field of Classification Search ........... 606/102; 422/33
See application file for complete search history.

(56) References Cited

U.S. PATENT DOCUMENTS 3,291,640 A    12/1966    Livingston
3,318,774 A    5/1967    Dingwall et al.
4,193,818 A    3/1980    Young et al.
4,294,753 A    10/1981    Urist
4,300,243 A    11/1981    Baumgartner
4,553,974 A    11/1985    Dewanjee
4,801,299 A    1/1989    Brendel et al.
4,871,366 A    10/1989    von Recum et al.

(Continued)

FOREIGN PATENT DOCUMENTS

EP    0 335 851    10/1989

(Continued)

OTHER PUBLICATIONS

Grood, E.S.; Noyes, F. R., Cruciate ligament prosthesis: strength, creep, and fatigue properties, Dec. 1976, The Journal of Bone and Joint Surgery, 58: 1083-1088.*

(Continued)

*Primary Examiner*—Elizabeth L McKane
*Assistant Examiner*—Regina Yoo
(74) *Attorney, Agent, or Firm*—McAndrews, Held & Malloy, Ltd.

(57) ABSTRACT

The present invention is directed to the field of implants that include soft tissue. More particularly, the present invention is directed to processes for treating implants that include soft tissues such as tendons and ligaments, and to implants produced by such processes. The present invention is also directed to processes and apparatus for improved processing of implants that include soft tissue, by applying kinematic restraint, preferably tension, to the implant or specific portions of the implants during the treatment, and to implants produced by such processes and apparatus. The present techniques yield soft tissue implants having superior structural, mechanical, and/or biochemical integrity.

40 Claims, 7 Drawing Sheets

1A

1D

1B

1E

1C

U.S. PATENT DOCUMENTS

| | | | |
|---|---|---|---|
| 4,890,457 A | 1/1990 | McNally et al. | |
| 4,950,296 A | 8/1990 | McIntyre | |
| 4,976,733 A | 12/1990 | Girardot | |
| 4,982,730 A | 1/1991 | Lewis, Jr. | |
| 5,037,437 A | 8/1991 | Matsen, III | |
| 5,066,578 A | 11/1991 | Wikman-Coffelt | |
| 5,095,925 A | 3/1992 | Elledge et al. | |
| 5,213,619 A | 5/1993 | Jackson et al. | |
| 5,232,857 A | 8/1993 | Lefevre et al. | |
| 5,288,462 A | 2/1994 | Carter et al. | |
| 5,298,222 A | 3/1994 | O'Leary | |
| 5,333,626 A | 8/1994 | Morse et al. | |
| 5,380,826 A | 1/1995 | Castor et al. | |
| 5,397,357 A | 3/1995 | Schmieding et al. | |
| 5,429,810 A | 7/1995 | Knaepler et al. | |
| 5,507,810 A | 4/1996 | Prewett et al. | |
| 5,509,968 A | 4/1996 | Carr | |
| 5,513,662 A | 5/1996 | Morse et al. | |
| 5,556,379 A | 9/1996 | Wolfinbarger et al. | |
| 5,556,428 A | 9/1996 | Shah | |
| 5,607,476 A | 3/1997 | Prewett et al. | |
| 5,711,921 A | 1/1998 | Langford | |
| 5,716,454 A | 2/1998 | Carr | |
| 5,723,012 A | 3/1998 | Fages et al. | |
| 5,725,579 A | 3/1998 | Fages et al. | |
| 5,753,195 A | 5/1998 | Langford et al. | |
| 5,769,893 A | 6/1998 | Shah | |
| 5,797,871 A | 8/1998 | Wolfinbarger, Jr. | |
| 5,820,581 A | 10/1998 | Wolfinbarger, Jr. | |
| 5,846,484 A | 12/1998 | Scarborough et al. | |
| 5,976,104 A | 11/1999 | Wolfinbarger, Jr. | |
| 5,977,034 A | 11/1999 | Wolfinbarger, Jr. | |
| 5,977,432 A | 11/1999 | Wolfinbarger, Jr. et al. | |
| 5,993,844 A | 11/1999 | Abraham et al. | |
| 6,001,106 A | 12/1999 | Ryan et al. | |
| 6,024,735 A | 2/2000 | Wolfinbarger, Jr. | |
| 6,102,056 A | 8/2000 | Kotsopey | |
| 6,206,931 B1 * | 3/2001 | Cook et al. | 623/23.75 |
| 6,235,239 B1 | 5/2001 | Sharma | |
| 6,290,718 B1 | 9/2001 | Grooms et al. | |
| 6,293,970 B1 | 9/2001 | Wolfinbarger, Jr. | |
| D461,248 S | 8/2002 | Bianchi et al. | |
| 6,440,444 B2 | 8/2002 | Boyce et al. | |
| 6,471,723 B1 * | 10/2002 | Ashworth et al. | 623/2.42 |
| 6,482,584 B1 | 11/2002 | Mills et al. | |
| 6,497,726 B1 | 12/2002 | Carter et al. | |
| 6,572,650 B1 * | 6/2003 | Abraham et al. | 623/1.38 |
| 6,613,278 B1 | 9/2003 | Mills et al. | |
| 6,652,592 B1 | 11/2003 | Grooms et al. | |
| 6,652,818 B1 | 11/2003 | Mills et al. | |
| 6,685,626 B2 | 2/2004 | Wironen | |
| 6,696,073 B2 | 2/2004 | Boyce et al. | |
| 6,699,252 B2 | 3/2004 | Farr, II et al. | |
| 2001/0018619 A1 * | 8/2001 | Enzerink et al. | 623/23.72 |
| 2001/0023372 A1 | 9/2001 | Chen et al. | |
| 2001/0031254 A1 | 10/2001 | Bianchi et al. | |
| 2002/0106393 A1 | 8/2002 | Bianchi et al. | |
| 2002/0165611 A1 * | 11/2002 | Enzerink et al. | 623/13.11 |
| 2003/0014126 A1 * | 1/2003 | Patel et al. | 623/23.72 |
| 2003/0229394 A1 * | 12/2003 | Ogle et al. | 623/2.14 |

FOREIGN PATENT DOCUMENTS

| | | | |
|---|---|---|---|
| EP | 0424159 | | 10/1990 |
| JP | 03/224570 | | 1/1990 |
| JP | 3-224570 | | 10/1991 |
| SU | 952189 | | 8/1982 |
| WO | WO 94/11035 | | 5/1994 |
| WO | WO 97/27882 | | 7/1997 |
| WO | WO 98/41245 | | 9/1998 |
| WO | WO 99/47080 | | 9/1999 |
| WO | WO 99/51170 | | 10/1999 |
| WO | WO 99/66967 | | 12/1999 |
| WO | WO 00/29037 | * | 5/2000 |
| WO | WO 01/26703 | | 4/2001 |

OTHER PUBLICATIONS

Piet, M.P.J., et al., The use of tri(n-butyl) phosphate detergent mixtures to inactivate hepatitis viruses and human immunodeficiency virus in plasma and plasma's subsequent fractionation, Transfusion vol. 30, No. 7, 1990, pp. 591-598.

Hellstern, et al., Vox Sang, 1992:63:178-185, Manufacture and in vitro Characterization of Solvent/Detergent-Treated Human Plasma.

Horowitz, B. et al., Solvent/Detergent-Treated Plasma: A Virus-Inactivated Substitute for Fresh Frozen Plasma.

Carr, James, et al. "A Feasability Study for Removing Tissue Contamination from Porous Implants." Biomedical Instrumentation and Technology. May/Jun. 1995. 220-225.

Levine, David, et al. "Cost Awareness and Containment for the 1990's: Recycling Orthopaedic Implants." Contemporary Orthopaedics, Oct. 1992. 25(4): 376-381.

American National Standard. "Good Hospital Practice: Handling and Biological Decontamination of Reusable Medical Devices." Association for the Advancement of Medical Instrumentation, 1991. 1-14.

Brown, John Stuart. "An Ultrasonic Cleaning Bath in General Practice." Practioner, Apr. 8, 1988. 232: 377.

University of Florida Tissue Bank, Inc. "Threaded Cotical Dowel: Processing and Screening Methods." Technical Monograph, 1996. 1-6.

Grafton Deminineralized Bone Matrix (DBM) "First Consider the Source: Musculoskeletal Transplant Foundation." Osteotech, Inc., 1995.

Wolfinbarger, et al. "A Comprehensive Study of Physical Parameters, Biomechanical Properties, and Statistical Correlations of Iliac Crest Bone Wedges Used in Spinal Fusion Surgery." Spine, 1994. 19(3): 277-283.

Stanford, C.M. et al. "Bone Cell Expression on Titanium Surfaces is Altered by Sterilization Treatments." J Dent Res, May 1994. 73(5): 1061-1071.

Evanoff, Jean. "Sterilizing and Preserving Human Bone." AORN Journal, Apr. 1983. 37(5): 972-980.

Petri, W.H., et al. "Demineralized Bone Sterilization." J Dent Res, 1993. 72 (IADR Abstracts) 417.

Bloom, D.S., et al. "Effects of Multiple Sterilization in the Monocortical Screw-Bone Interface." J Dent Res, 1996. 75 (IADR Abstracts) 335.

Liu, Yu et al. "Detergent Treatment on Canine Tracheal Allograft." Transplantation, 1999. 67(9): S649.

Voggenreiter, G. et al. "Effects of Preservation and Sterilization on the Biomechanical Properties of Cortical Bone Grafts." J. Biomechanics, 1991. 24(6): 458.

Mschvidobadse, Von M.V. "Allogenic Transplantation of Sterilized Bones and Halfjoints." Zbl. Chirurgie, 1978. 103: 1138-1148.

American Red Cross, "Aseptically-Processes Bone and Connective Tissue." ARC, North Central Region, 1995.

Database WPI, Section PQ, Week 199429, Dewetn Publications, Ltd., London, GB; AN 1994-239698, XP002135434 & SU 1 811 817 A (Traumatology Orthopaedy Res Inst.), Apr. 30, 1993 abstract.

Maddox, Ewa, et al. "Optimizing Human Demineralized Bone Matrix for Clinical Application" Burgess, 529-534.

Conrad, et al., The Effects of Freeze-Drying and Rehydration on Cancellous Bone, *Clinical Orthopaedics and Related Research*, No. 290, pp. 279-284 (1993).

West, et al., Ultrasound Debridement of Trabeculated Bone: Effective and Atraumatic, *Plastic and Reconstructive Surgery*, pp. 561-566, Mar. 1994.

Frozen Bone & Soft Tissue Allograft, Instruction Sheet, 1994 California Transplant Services, Inc. (Oct. 1994).

von Versen, et al., The peracetic acid/low pressure cold sterilization—A new method to sterilize corticocancellous bone and soft tissue, *Z exp. Chir. Transplant Künstl.* pp. 18-21, Organe 22 (1989).

International Search Report dated Dec. 9, 2004 for PCT/USO4/12312.

* cited by examiner

PROCESS AND APPARATUS FOR TREATING IMPLANTS COMPRISING SOFT TISSUE

FIELD OF THE INVENTION

The present invention is directed to the field of implants comprising soft tissue. More particularly, the present invention is directed to processes for treating implants comprising soft tissues such as tendons and ligaments, and to implants produced by such processes. The present invention is also directed to processes and apparatus for improved processing of implants comprising soft tissue, by applying kinematic restraint, preferably tension, to the implant or specific portions of the implant, and to implants produced by such processes and apparatus. The present techniques yield soft tissue implants having superior structural, mechanical, and/or biochemical integrity.

BACKGROUND OF THE INVENTION

Implants comprising soft tissues may be implanted into a recipient to replace and/or repair existing soft tissues. For example, hereditary defects, disease, and/or trauma may damage soft tissues such that replacement and/or repair is desirable. These implants may be allografts, autografts, or xenografts, and the recipients may be human, mammal, or animal recipients. Implants are frequently used where the recipient is a human patient. Implants comprising soft tissues have been used, including in human patients, to replace heart valves, ligaments, tendons and skin, among other tissues.

It is desirable to treat implants, particularly autografts, allografts, and xenografts, to remove one or more undesirable components or to instill one or more desirable components. For example, implants may be passivated, or treated to remove or inactivate bacteria, viruses, fungi and other pathogens and antigenic constituents.

It is also well known to treat implants including implants comprising soft tissues with cleaning agents and/or gamma radiation. However, existing techniques suffer from one or more disadvantages. Undesirable results from radiation can include formation of radicals, hydrogen, and low-molecular-weight hydrocarbons; increased unsaturation; discoloration; and oxidation. The use of some chemical sterilizing agents (for example, glutaraldehyde) increases the risk that a toxic response will be evoked. Furthermore, some chemical sterilizing agents (for example, peroxides) may damage the implant, particularly soft tissues, which tend to be somewhat more fragile than bone and hard tissues. A particular concern with the passivation of implants comprising soft tissues is that treated soft tissue may suffer from increased laxity, reduced stiffness, reduced strength, or reduced biocompatibility, which can lead to variable performance of the implant. It is desirable to have treatment processes, including a process for passivation, that does not cause excessive laxity or reduction in stiffness or strength or biocompatibility of the soft tissue.

There is a continuing need in the art for a method of passivating implants comprising soft tissues that minimizes the possibility of immune rejection or infection. Further, there is a need in the art for a method of passivating implants comprising soft tissues which does not excessively damage the soft tissues. There is also a need for a method of passivating soft tissues that is quick, efficient, and results in a soft tissue with acceptable performance characteristics. U.S. Pat. No. 6,024,735 ("the '735 patent") (LifeNet)—"Process and composition for cleaning soft tissue grafts optionally attached to bone and soft tissue and bone grafts produced thereby," is directed to a method and composition for cleaning cadaveric soft tissue optionally attached to bone to produce soft tissue grafts optionally attached to bone suitable for transplantation into a human. The method involves removing bone marrow elements, blood deposits and any bacteria, virus or fungi contamination, from the donor bone and/or associated soft tissues. The '735 patent discloses a process in which bone graft and associated soft tissue is contacted with a first solvent that may include an alcohol, and a second solvent that may include hydrogen peroxide or an alcohol (col 14, line 65 to col. 16, line 34, and col. 17, line 53 to col. 18, line 56). Optional components (including hydrogen peroxide) may be added to either the first, second, third, or any subsequent solvents. (Id.) However, this process does not address damage from peroxide nor does it teach any method of protecting the tissues from such damage. Furthermore, the '735 patent states: "The order of use of solvents and the particular compositions of a particular solvent used in the present process is not critical as long as the first solvent used is a solvent containing one or more detergents." (col. 17, lines 13-16).

U.S. Pat. No. 5,797,871 ("the '871 patent") (LifeNet)—"Ultrasonic Cleaning of Allograft Bone," is directed to a method for cleaning cadaveric donor bone to produce bone grafts suitable for transplantation into a human, as well as the bone grafts produced thereby. The method involves removing bone marrow potentially containing bacteria, virus or fungi, from the donor bone by sonicating the bone in a solvent containing one or more detergents to produce bone grafts essentially free from bone marrow. The solvent may contain, but is not limited to, one or more of the following: sterile water; saline; a detergent; an alcohol, for example, ethanol and/or isopropanol, solvents, a combination of solutes desired to facilitate solubilization of bone marrow; chelating agent; virucidal agent; bactericidal agent; antimycotic agent; sodium hydroxide or similar strong base, organic and/or inorganic acid and hydrogen peroxide. The '871 patent also discloses the use of decontaminating agents including, but not limited to, one or more of an antibacterial agent; an antiviral agent; an antimycotic agent; an alcohol for example, methyl, ethyl, propyl, isopropyl, butyl, and/or t-butyl; trisodium phosphate; sodium hydroxide; hydrogen peroxide; and/or any detergent. The '871 patent states that soft tissue debridement is not an essential element of the bone cleaning technology, but the '871 patent does not state that its cleaning method is suitable for cleaning soft tissues, nor does it address the issue of steriliant damage to soft tissues, not does it discuss methods of protecting soft tissue from such damage.

U.S. Pat. No. 5,769,893 ("the '893 patent") (Shah) (which is a continuation-in-part application of U.S. Pat. No. 5,556,428) discloses an apparatus and method for inducing growth of soft tissues including skin, ligaments, tendons, blood vessels, and spinal cord which includes a tensioned spring causing the application of force on the soft tissue in the direction of the desired growth. The device also includes means for attaching the tensioned spring to the tissue and means for maintaining tension on the spring as the tissue grows. Further, a monitoring and control device can be included which can monitor and control the amount of growth.

U.S. Pat. No. 5,397,357 ("the '357 patent") (Arthrex)—"Method For Preparing A Bone-Tendon-Bone Core Graft", discloses a method for preparing a bone-tendon-bone core graft. A bone core is harvested from a patient and divided into two separate bone core halves. The bone core halves are inserted onto holding pins which are movably spaced along a work station. A harvested tendon is secured with suture onto the bone core halves, with the tendon extending therebetween to form the bone-tendon-bone core graft. The holding pins are supported by blocks which are moved apart along the work station to tension the bone-tendon-bone graft.

U.S. Pat. No. 5,333,626 ("the '626 patent") (Cryolife)—"Preparation of Bone for Transplantation", relates to a method of preparing bone for transplantation by maintaining the internal matrix of the bone to be implanted, preferably at high pressure, in the presence of a decontaminating agent, preferably polyvinyl pyrrolidine-iodine (PVP-I) optionally in the presence of a detergent, in solution. The '626 patent discloses a variety of other decontaminating agents which have been found to inactivate a wide range of infectious agents including bacteria, fungi, parasites and virus: hydrogen peroxide, ethanol, ozone, ethylene oxide, irradiation and mixtures thereof and with PVP-I. Although the '626 patent discloses that its procedure may be applied to bone blocks with attached connective tissue, it states that the connective tissue should not be subjected to the cleaning procedures: "If bone blocks with attached connective tissue are to be cleaned, the connective—tissue tendons, ligaments, menisci, for example—should be covered with a sterile covering such as plastic wrap or sterile drape during the cleaning procedure." (col. 5, line 41-45).

U.S. Pat. No. 6,293,970 ("the '970 patent") (Culp)—"Plasticized bone and soft tissue grafts and methods of making and using same," is directed to a plasticized dehydrated or freeze-dried bone and/or soft tissue product. Water in the molecular structure of the bone or soft tissue matrix is replaced with one or more plasticizers. Permeation enhancers such as isopropanol may be used to facilitate permeation of plasticizer into bone or soft tissue. (col. 7, line 17).

Tissue sterilization methods known in the art have undesirable attributes. Gamma irradiation, in order to ensure destruction of pathogens, such as the human immunodeficiency virus (HIV), has been used at doses that result in tissue destruction (e.g. 3.5 Mrad; see, for example, Rasmussen, et al., J. Arthroscopic and Related Surgery, 10(2):188-197, (1994); Goertzen, et al., British Soc. of Bone and Joint Surg., 77:204-211 (805); Loty, et al., International Orthopaedics, 14:237-242, (1990)). Use of ethylene oxide has been found to result in implants that produce inflammatory responses (Kudryk, et al., J. Biomedical Materials, 26:1477-1488, (1992); Thoren, et al., Clin. Orthopaedics, 318:259-263, (1995); Simonian, et al., Clin. Orthopaedics, 302:290-296, (1994); Jackson, et al., Am. J. Sports Medicine, 18:1-9, (1990)). Standard chemical solution treatments, while effective in sterilizing surfaces with which the solutions are brought into contact, tend to be insufficiently penetrating to reach the interstices of tissues, where potentially pathogenic organisms may reside. With regard to sterilization of soft tissue, the potential for damage to the soft tissue by irradiation, ethylene oxide, or chemical solution treatment is of particular concern, because soft tissue are more susceptible to damage than bone tissue. Even milder sterilants such as peroxides may cause damage due to swelling of the tissues and the presence of residual reaction byproducts.

A desirable treatment process includes one or more of the following features: Effective removal or inactivation of a wide range of bacterial, viral and fungal pathogens; absence of graft toxicity; retention of desirable tissue characteristics, such as biomechanical strength or growth-inducing properties; effectiveness across a wide range of operating modifications and for a wide variety of tissue types; ability to conclude the process in a final implant tissue container, to ensure sterile packaging and delivery for implantation; ability to apply automated control and monitoring systems and develop an automated and validated process.

SUMMARY OF THE INVENTION

The present invention is directed to processes and apparatus for making an implant comprising soft tissue more suitable for implantation into a recipient. Soft tissues (such as tendons and ligaments) treated according to the present techniques are wholly or partially passivated by contact with cleaning agents, such as a solution containing an oxidizing sterilant (for example, hydrogen peroxide). The tissues are protected from damage from the oxidizing sterilant by contacting the tissues with a protective agent, such as an alcohol, and/or by application of kinematic restraint, such as tension. Those soft tissues tend to have superior structural, mechanical, and/or biochemical integrity and experience less collagen damage attributable to such contact with the oxidizing sterilant. Indeed, the application of tension to the implant while it is contacted with cleaning agents (such as a detergent, an alcohol, or a peroxide) can reduce the damage attributable to the cleaning agents.

As a first aspect, a process is provided for making an implant more suitable for implantation into a recipient. At least part of the implant is a soft tissue. The process comprises: (a) contacting the implant with a protective agent, such as an alcohol; (b) contacting the implant with an oxidizing sterilant, such as a peroxide; and (c) contacting the implant with a rinsing agent, which at least partially rinses the oxidizing sterilant from the implant.

As another aspect, a process for making an implant more suitable for implantation into a recipient is provided. The implant at least partially comprises a soft tissue, and the process comprises contacting the implant with an oxidizing sterilant such as a peroxide for less than about 120 consecutive minutes, alternatively no more than about 100 consecutive minutes, alternatively no more than about 80 consecutive minutes, alternatively no more than about 60 consecutive minutes, alternatively no more than about 40 consecutive minutes, alternatively no more than about 30 consecutive minutes, alternatively no more than about 20 consecutive minutes, alternatively no more than about 10 consecutive minutes, alternatively no more than about 5 consecutive minutes, alternatively no more than about 60 consecutive seconds, alternatively no more than about 40 consecutive seconds, alternatively no more than about 20 consecutive seconds, alternatively no more than about 10 consecutive seconds. Each step comprising a consecutive contact time may be followed or preceded by one or more steps comprising contacting the implant with a rinsing fluid, such as sterile water, saline, a protective agent, such as alcohol, a detergent, or any combination thereof As another aspect, a process for making an implant more suitable for implantation into a recipient is provided. The implant at least partially comprises a soft tissue, and the process comprises contacting the implant with an oxidizing sterilant such as a peroxide for less than about 240 cumulative minutes, alternatively less than about 120 cumulative minutes, alternatively less than about 90 cumulative minutes, alternatively less than about 80 cumulative minutes, alternatively no more than about 60 cumulative minutes, alternatively no more than about 40 cumulative minutes, alternatively no more than about 20 cumulative minutes, alternatively no more than about 10 cumulative minutes. The total contact time may be accumulated through a number of individual contact steps, each of which may be separated by one or more steps comprising contacting the implant with a rinsing fluid, such as sterile water, saline, a protective agent, such as alcohol, a detergent, or any combination thereof.

As yet another aspect, a process for treating an implant comprising a soft tissue so as to clean the implant prior to implantation is provided. The process comprises applying kinematic restraint to the implant comprising the soft tissue while contacting the soft tissue with a cleaning agent. Preferably, the kinematic restraint comprises tension applied to the soft tissue in one or more degrees of freedom. Alternatively, the kinematic restraint comprises compression applied to the soft tissue in one or more degrees of freedom.

As yet another aspect, a process is provided for making an implant more suitable for implantation into a recipient. At least part of the implant is a soft tissue, and the process comprises applying tension to the implant, perfusing the tensioned implant with an alcohol, and perfusing the tensioned implant with a peroxide. The process may also comprise perfusing the tensioned implant with other cleaning agents. Such perfusing steps may be performed for periods comprising the numbers of cumulative and/or consecutive minutes set forth above. Preferably, the implant is perfused with a protectant such as isopropanol against oxidation damage before and after the implant is perfused with an oxidizing sterilant.

In the foregoing processes, the implant can be contacted with the oxidizing sterilant at a temperature greater than 42° C., alternatively greater than 44° C., alternatively greater than 46° C., alternatively at a temperature of at least about 48° C. The foregoing-processes may also include the step of applying tension to the soft tissue at least during part of a period of contact with an oxidizing sterilant. The implant can be contacted with the oxidizing sterilant and alcohol in one or more additional steps, and the oxidizing sterilant and alcohol steps may be separated by contact with water or other cleaning agents. Preferably, prior to and/or subsequent to the oxidizing sterilant contact, the implant contains an amount of the alcohol in the soft tissue sufficient to reduce oxidation damage to the soft tissue. For example, it is contemplated that the implant may contain an alcohol in an amount of at least about 1 weight percent, alternatively at least about 2 weight percent, alternatively at least about 5 weight percent, alternatively at least about 8 weight percent, alternatively at least about 12 weight percent, before contact with the oxidizing sterilant. It is also contemplated that implants and portions of implants that are less porous and/or more dense (such as, for example, tendon) will tend to require lesser amounts to reduce damage, while those that are more porous and/or less dense (such as, for example, muscle) will tend to require greater amounts to reduce damage. For example, it is contemplated that a less dense and/or more porous implant may contain an alcohol in an amount of at least about 10 weight percent, alternatively at least about 20 weight percent, alternatively at least about 40 weight percent, alternatively at least about 60 weight percent, alternatively at least about 80 weight percent, before contact with the oxidizing sterilant. The effective amounts for a given implant type will be easily determinable with routine experimentation in view of the present disclosure.

As a further aspect, an apparatus for applying kinematic restraint to an implant is provided. As exemplary embodiments of such an apparatus, tissue tensioners are described in detail herein, but apparatus that apply a kinematic restraint other than tension (such as compression or immobilization) to the tissue will have utility as well, as also described herein. The apparatus comprises (a) fasteners adapted to securely hold first and second ends of an implant, and (b) a resilient member disposed between the two fasteners. The resilient member can be adjusted to accommodate the size or shape of the implant and/or to apply a controlled force, torque, displacement, or orientation to the implant.

When the apparatus is a tissue tensioner, the resilient member will be selected from the group consisting of coil springs, leaf springs, torsional springs, flexible plastic members, and assemblies or combinations thereof. The resilient member will act upon the fasteners so as to force the fasteners apart. When ends of an implant are attached to the fasteners, and the fasteners are forced apart by the resilient member, tension (a preferred species of kinematic restraint) is applied to the implant.

The apparatus can also include a shaft disposed between the fasteners, where the fasteners are slidable along the shaft. The apparatus can also include a locking mechanism that locks one of the fasteners at a desired point along the shaft. The apparatus can also include a channel, and the locking mechanism can be a screw adapted to engage the channel of the shaft. The channel can have teeth adapted to engage the screw. The apparatus can also include a visual indicator adapted to indicate a predetermined tension of the resilient member is achieved.

The tissue tensioner apparatus may be used in conjunction with the foregoing processes for making an implant more suitable for implantation into a recipient, or the apparatus may be used with another process for treating (for example, other processes for cleaning, sterilizing and/or passivating) an implant comprising a soft tissue.

The apparatus for applying kinematic restraint can be adapted to provide kinematic restraint to the implant throughout one or more steps of recovery, processing, packaging, shipment, storage, preoperative preparation of the implant, interoperative preparation of the implant, and interoperative handling of the implant. Accordingly, processes are provided for providing kinematic restraint to a implant comprising a soft tissue, the process comprising loading an implant on one of the apparatus described herein, and providing kinematic restraint to the implant throughout one or more steps of recovery, processing, packaging, shipment, storage, preoperative preparation, intraoperative, and intraoperative handling of the implant.

A packaging apparatus for an implant comprises a kinematic restraint apparatus and a packaging material for sterile packaging of an implant, and the restraint and the implant are disposed inside the packaging material. The packaging material can comprise a means for holding the restraint or the implant in a predetermined place, such as snaps, detents, slots, holes, pins, hooks, clips, protrusions, and the like, and combinations thereof.

The foregoing processes and apparatus may be employed in the cleaning, sterilization and/or passivation of implants comprising soft tissues. The foregoing processes will typically include perfusing the implant with the cleaning agents by cyclically increasing and decreasing pressure during the contact of the cleaning agent with the implant. In preferred embodiments, a treatment chamber containing the implant to be treated is filled with the cleaning agent (typically provided as a solution containing the cleaning agent in some concentration). While the implant is immersed in a cleaning agent solution, the pressure in the treatment chamber is cyclically increased and decreased during the contact of the cleaning agent with the implant. By cyclically increasing and decreasing pressure, the cleaning agent is made to perfuse into the implant. Deep, penetrating cleaning, sterilization and/or passivation of the implant or portions thereof are achieved by the rate of pressure cycling, the fact of cycling, and possibly the amplitude of pressure cycling.

When cycling pressures are employed, the increased pressure may be as high as about 200 pounds per square inch (PSI) above ambient pressure, alternatively about 150 PSI above ambient pressure, alternatively about 100 PSI above ambient pressure, and it may be as low as about 75 PSI above ambient pressure, alternatively about 50 PSI above ambient pressure, alternatively about 25 PSI above ambient pressure, alternatively about 15 PSI above ambient pressure, alternatively about 5 PSI above ambient pressure. Higher pressures may be contemplated by the process, though it is desirable to avoid pressures that would lead to equipment failure or tissue damage due to such pressures. The decreased pressure may be as high as about ambient pressure, alternatively about 4 PSI below ambient pressure, or may be as low as about 8 PSI below ambient pressure, alternatively about 12 PSI below ambient pressure, alternatively about 14 PSI below ambient pressure. Any high pressures and low pressures, as specified above, may be combined to define a range of pressures, providing that the minimum selected is equal to or less than the maximum selected. The term ambient pressure will be understood by those skilled in the art to apply to either the nominal atmospheric pressure at the location where the process is practiced, or any suitable reference pressure which may be used as a reference for measurement of pressure within the reaction chamber for a given instance of the process. When rapidly cycling increased and decreased pressures are employed, the rate of pressure cycling can be at least about 1 second, alternatively at least about 2 seconds, alternatively at least about 5 seconds, alternatively at least about 10 seconds, alternatively at least about 20 seconds, alternatively at least about 30 seconds, alternatively at least about 50 seconds, alternatively at least about 60 seconds, alternatively at least about 120 seconds, alternatively at least about 180 seconds, alternatively at least about 240 seconds. When rapidly cycling pressures are employed, the rate of pressure cycling can be at most about 5 minutes, alternatively at most about 4 minutes, alternatively at most about 3 minutes, alternatively at most about 2 minutes, alternatively at most about 110 seconds, alternatively at most about 100 seconds, alternatively at most about 90 seconds, alternatively at most about 60 seconds, alternatively at most about 45 seconds, alternatively at most about 30 seconds, alternatively at most about 20 seconds, alternatively at most about 10 seconds. Any maximum and minimum rates, as specified above, may be combined to define a range of rates, providing that the minimum selected is equal to or less than the maximum selected.

Treatment processes may be successfully conducted at pressures above or below one atmosphere. Evacuation pressures between 25 inches of mercury (about 85 kPa or about 12.5 PSI) and the vapor pressure of the solutions in the chamber are adequate. Backfill pressures of between about 40 and 100 PSI (between about 276 kPa and 690 kPa or between about 80 and 200 inches of mercury) are also adequate. The use of rapidly cycling pressures are described in U.S. Pat. Nos. 6,482,584; 6,613,278; and 6,652,818; each of which issued to the present assignee, and each of which is hereby incorporated by reference.

In one embodiment, the entire process is conducted in a chamber which permits for sonication of the contents throughout or at particular stages of the process. In addition, preferably, the entire process is conducted in a programmable system under computer or programmable logic circuit control, so that manual processing is minimized and reproducibility of the process is maximized. Where the processed tissue is a bone implant or any form of allograft or xenograft tissue, election of appropriate solvents, such as urea (preferably about 6 M), or other chaotropic reagents (e.g. 4 M guanidine hydrochloride, or the like), has the additional advantage of producing a processed tissue of even lower antigenicity than if such treatment were not included. Target decontamination goals for the treatment process include:

Between about a one (1) to twelve (12) log reduction in bacterial contamination;

Between about a one (1) to fifteen (15) log reduction in enveloped virus contamination;

Between about a one (1) to five (6) log reduction in non-enveloped virus contamination;

Between about a two (2) to ten (10) fold reduction in endotoxin;

Maintenance of implant or graft biologic and biomechanical properties;

Absence of tissue toxicity due to cleaning agents used; and

Reduced implant antigenicity.

Such treatments and desirable results may also be applied to treatment of diseased tissue which may be harvested, treated ex vivo, and re-implanted.

BRIEF DESCRIPTION OF SEVERAL VIEWS OF THE DRAWINGS

FIG. 1(a) through (e) shows various views of an implant comprising a soft tissue. More particularly.

DETAILED DESCRIPTION OF THE INVENTION

Figure 1:
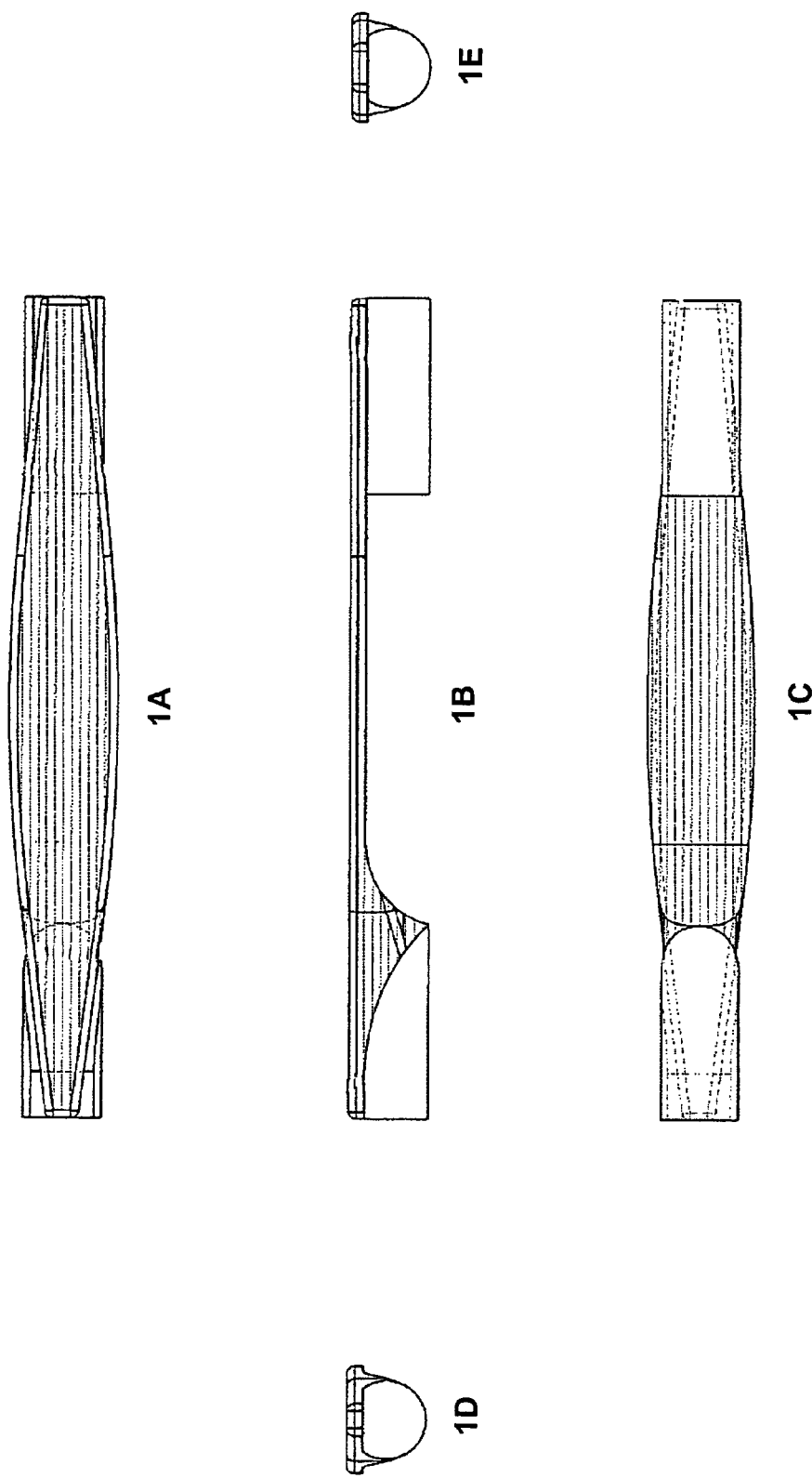
FIG. 1 shows a bone-tendon-bone implant which may be treated according the present techniques.

Soft tissue, as used herein, refers to any biological tissue other than bone, including but not limited to tendons, ligaments, fascia, whole joints, dura, skin, pericardia, heart valves, veins, neural tissue, submucosal tissue (e.g. intestinal tissue), and cartilage.

Implant, as used herein, refers to any material the implantation of which into a human or an animal is considered to be beneficial. Accordingly, the implant may be tissue-derived material, such as bone, skin, and the like, or it may be a metallic or synthetic material having an external surface or internal structure that may require cleaning, sterilization or passivation. An implant may comprise autograft tissue, allograft tissue, xenograft tissue or combinations thereof, and in the case of mineralized tissues, such as bone, the implant may comprise mineralized tissue, partially demineralized tissue, completely demineralized tissue, and combinations thereof. The implant may comprise unitary or monolithic graft material, assembled bone materials such as those described in U.S. patent application Ser. Nos. 09/782,594 and 09/941,154, shaped implants such as those described in U.S. Pat. Nos. 6,440,444 and 6,696,073, and allogeneic biocompatible matrices such as those described in U.S. patent application Ser. Nos. 10/754,310 and 10/793,976. The present processes and apparatus may also be employed in the treatment of implants such as those described in U.S. Pat. Nos. D461,248; 6,290,718; 6,497,726; 6,652,592; 6,685,626; and 6,699,252. All of the foregoing patents and patent applications are incorporated by reference herein.

Kinematic restraint, as used herein, refers to control over the physical position and/or orientation of the implant and may include tension, compression and/or immobilization of the implant or any specific portions of the implant. Preferably, the kinematic restraint applied to the implant comprises tension applied to the soft tissue of the implant. Suitable kinematic restraint apparatus may provide axial and/or radial restraint or tension to an implant or provide tension or restraint to an implant in one, two or three dimensions. Kinematic restraint applied to an implant may include tension, compression, or immobilization applied to the implant, preferably to the soft tissue of an implant. Kinematic restraint provides control of position, orientation, motion, or stresses of the implant comprising the soft tissue in from 1 to 6 degrees of freedom.

Passivation, as used herein, refers to the elimination, reduction, or inactivation of potentially pathogenic organisms, such as spores, germs, bacteria, and other microorganisms, and immunogenic substances from an implant. Thus, sterility, sporicidal effect, pathogen inactivation and/or removal, and reduced antigenicity are intended by this term, although elimination of beneficial biological properties of the implant is not intended by this term. The term passivation is preferred to the term sterilization because, while sterilization is a goal, that term has an absolute connotation which can rarely, if ever, be completely achieved without attendant tissue destruction. In addition, while the implants produced according to the present processes may not be completely devoid of any antigenicity or pyrogenicity, these undesirable aspects are greatly reduced, and this too is intended by the term passivation, as used herein. Reduced antigenicity promotes accelerated healing potential. Thus a passivated implant, with inherently reduced risks of infection or disease transmission, minimized inflammatory response, and accelerated healing potential is preferred for implantation.

Perfused or perfusion, as used herein, are intended to imply efficient interpenetration of cleaning agents or biologically active substances into and through the channels and crevices of materials intended for implantation into a recipient.

Rapid and rapidly, as they are applied to pressure cycling herein, refer to time frames on the order of seconds to minutes, rather than hours or days.

Sonicate and sonication, as used herein, refer to the application of sonic or ultrasonic energy. Sonication may be applied via a container of an implant undergoing processing according to the present processes under conditions that permit efficient transfer of the sonic energy to the implant. Those skilled in the art are familiar with the process of sonication and conditions whereby sonic energy may be transferred through a fluid to a workpiece such that efficient cleaning and bacterial or cellular disruption is achieved, without resulting in gross, ultrastructural damage to the workpiece.

Novel processes are provided for processing implants comprising soft tissue including, but not limited to, bone and soft tissue, mineralized or demineralized tissues and combinations of the foregoing types of tissues. In particular, soft tissue treated according to the present processes permit soft tissue to be thoroughly cleaned, sterilized, and/or passivated, without excessive structural or chemical damage to the soft tissue.

While the inventors do not intend to be bound by theory, it is presently theorized that damage to soft tissues from various treatment processes may arise from collagen degradation. Such collagen degradation may be caused by chemical exposure to cleaning agents typically used in the cleaning and sterilization of soft tissue. Example 1 identifies chemical and physical process parameters found by the inventors to affect soft tissue strength. As described below, the inventors have found that damage to collagen by an oxidizing sterilant (for example, peroxide) poses a significant concern. The present techniques provide ways to reduce such oxidation damage.

In view of the Background review of the known art relating to implant treatment and sterilization processes, it is believed that the present techniques provide an improvement in that implants comprising soft tissues may be treated (for example, cleaned, sterilized or passivated) with reduced damage. A number of methodologies are provided, the additive effect of which is the production of highly cleansed, passivated soft tissues, which may be implanted, without causing toxicity to the recipient and which will have good clinical performance. Various embodiments of the present processes include most or all of the above listed features, namely: effective removal or inactivation of a wide range of bacterial and viral pathogens; absence of graft toxicity; retention of desirable tissue characteristics, such as biomechanical strength or growth-inducing properties; effectiveness across a wide range of operating modifications and for a wide variety of soft tissue types; ability to conclude the process in a final implant tissue container; to ensure sterile packaging and delivery for implantation; ability to apply automated control and monitoring systems and develop an automated and validated process. Furthermore, in certain embodiments, one or more biologically active agents, or combinations of such agents, are infused into implants. In view of the use of the term implant herein, those skilled in the art will appreciate that an implant according to this invention may generally comprise autograft tissue, allograft tissue, xenograft tissue or combinations thereof; and may specifically comprise tendons, ligaments, fascia, whole joints, dura, skin, pericardia, heart valves, veins, neural tissue, submucosal tissue (e.g. intestinal tissue), and cartilage.

The present processes may be used in conjunction with other techniques for reducing the likelihood of providing implants having undesirable components therein. For example, methods for minimizing the risk that pathogenic donor tissue will be harvested and processed by a tissue bank, referred to herein as donor qualification, are known in the art. Accordingly, thorough donor screening, and tissue testing by enzymatic, immunological, biochemical and molecular biological techniques are applied to minimize the risk that tissue carrying pathogens (viruses, bacteria, and the like) will be included in the materials processed and made available for implantation. Testing for contamination by human immunodeficiency virus, HIV, hepatitis B virus, HBV, hepatitis C virus, HCV, has now become routine in the art. Known screening and qualification methods are desirably included as an initial step preceding processing of the implant material according to the present processes. None of these screening methods are 100% percent reliable, however, as is evidenced by recent cases involving allograft disease transmission. *Morbidity and Mortality Weekly Report*, U.S. Department of Health and Human Services, Centers for Disease Control and Prevention, Dec. 5, 2003 ("Although allograft infections are rare, they highlight the need for improved tissue evaluation and processing standards."). Due to the highly efficient implant treatment processes disclosed herein, it is further expected that as yet unidentified potentially pathogenic organisms or organisms for which routine testing has yet to be developed may be removed from implants by virtue of the present treatment processes. Redundancy in the level of implant cleaning that is built into the present passivation processes ensures removal and inactivation of such organisms or potentially pathogenic factors while at the same time permitting efficient implant processing.

For purposes of the following description, bone-tendon-bone ("BTB") graft is referred to as an exemplary soft tissue implant, and it comprises soft tissue that may be successfully processed according to the present techniques with reduced oxidation damage compared to prior techniques. FIG. 1 (a) through (e) shows a bone-tendon-bone implant which may be treated according the present techniques. FIG. 1(a) shows a top view, FIG. 1(b) shows a side view and FIG. 1(c) shows a bottom view. The bone-tendon-bone graft is a patellar tendon with bone blocks from the patella and tibia attached. FIG. 1 (d) shows the patella bone block and FIG. 1 (e) shows the tibia bone block. Though the present techniques will frequently be described in connection with a bone-tendon-bone graft, those skilled in the art will recognize that other implants, including but not limited to various soft tissues and combinations of bone and soft tissue, may be processed according to the principles defined herein, without departing from the spirit of the invention exemplified herein by reference to BTB. Those skilled in the art will appreciate that an implant according to this invention may comprise a great number of hard and soft autograft tissues, allograft tissues, xenograft tissues or combinations thereof.

According to the present processes, allograft material from qualified donors may be first treated by various known bioburden reducing methods. Subsequent to the optional steps of initial bioburden reduction and surface cleaning, the implant material may be further processed whereby bone marrow, blood, proteins, and particulate matter is efficiently removed, such that what remains is essentially a biological matrix, in which about a 5 to 6 log reduction in any form of viable organisms (viruses, bacteria, amoebae, rickettsia, fungi) is achieved. As described in greater detail below, this is achieved by a process of pressure cycling or oscillation, employing a variety of cleaning and sterilization solutions which are caused to efficiently interpenetrate the matrix. By repeated cycling and changing of the cleaning solvents, the channels of essentially any porous matrix are unclogged, and cleansed. A pre-defined, pre-programmed cycle of washes can be employed, preferably with concurrent ultrasonic bombardment, to achieve penetrating sterilization of the implant. We have found that the combination of oscillating fluid pressure and ultrasonic energy accelerates solution interpenetration and endogenous substance removal.

After being medically released (which can include passing a battery of risk factor and biochemical assays, including, for example, HIV-specific PCR, and the like), donor tissue can be cleaned of any extraneous or adventitious tissue. The cleaned tissue is loaded into a sealable reaction chamber. A preferably pre-programmed tissue cleaning process is then initiated comprising a plurality of wash steps. Deep tissue interpenetration by cleaning agents is achieved by oscillating the pressure in the chamber while the implant is immersed in various cleaning agents. Ultrasonic energy may be applied at various stages of the cleaning process to accelerate cleaning agent penetration and removal of unwanted contaminants or endogenous substances, including blood, lipid, and non-structural or undesired proteins.

The present processes comprise a novel sequence of cleaning agents which have surprisingly been found to protect the tissue from damage associated with known processing methods, for example damage to collagen. It has been surprisingly found that contacting a soft tissue with an alcohol before contacting the soft tissue with a peroxide, and contacting the soft tissue with an alcohol after contacting the soft tissue with a peroxide, can yield a passivated soft tissue having less damage attributable to the peroxide contact than a soft tissue contacted with peroxide according to conventional methods. Moreover, it has surprisingly been found that less damage arises from contact with a peroxide when tension is applied to a soft tissue than when no tension is applied, as in conventional methods. Thus, it is contemplated within the scope of the present invention that contact with peroxide or other oxidizing sterilant (or other cleaning agent) may occur while the implant is under tension. It is further contemplated that the implant may be contacted by an alcohol both before and after contact with a peroxide or another oxidizing sterilant.

In preferred embodiments of the present processes, one or more of the cleaning agents are contacted with the implant comprising the soft tissue to remove blood, fat, bacterial, viral, fungal or other contamination. Cleaning agents (and methods of using such cleaning agents) are described in U.S. Pat. Nos. 6,482,584; 6,613,278; and 6,652,818. Cleaning agents include detergents, disinfectants (sometimes called disinfecting agents), decontaminants (sometimes called decontaminating agents), antibiotics, virucidal compounds, and the like. The cleaning agents may be provided in the form of solutions or other mixtures. Preferably, the cleaning agent is provided as an aqueous solution. For example, one or more of the following cleaning agents can be contacted with an implant comprising a soft tissue as part of a passivation process(cleaning agents and methods of using such cleaning agents) are described in U.S. Pat. Nos. 6,482,584; 6,613,278; and 6,652,818: Triton X-100/TNBP, a solvent/detergent to remove debris and kill viruses and bacteria (cleaning agent B); 3% hydrogen peroxide, to remove cellular debris, inactivate viruses and bacteria (cleaning agent C); mixture of cleaning agents B and C (cleaning agent D); or water-miscible alcohol, such as ethanol or isopropanol (cleaning agent E); and mixtures of B, C, D, E in any desirable proportions.

However, in accordance with the present techniques, both before and after a cleaning agent comprising peroxide (such as cleaning agent C) is applied to the soft tissue, the soft tissue is kinematically restrained by tensioning and/or contacted with an alcohol. A kinematic restraint may be applied as a single restraint or as multiple restraints. The kinematic restraint may be applied before, during and/or after contact with the cleaning agent. The kinematic restraint may be applied in a constant manner or variable manner, for in a steady state or time variable manner.

More particularly, a pressurizable treatment chamber is loaded with the implant comprising soft tissue, optionally a soft tissue to which tension is being applied (as described in more detail below). The implant optionally includes metallic, synthetic or other man-made implant materials, autograft or allograft bone and soft tissue, xenograft bone and soft tissue, from a donor. It will further be understood that the implant may comprise soft tissue alone or a combination of soft tissue and bone and/or synthetic materials.

A cleaning agent (such as one or more of cleaning agents B, C, D, E and mixtures thereof) is introduced to the treatment chamber. A sufficient amount of cleaning agent will usually be introduced so as to immerse the implant (in other words, the implant is submerged within the cleaning agent). In the presence of the cleaning agent and optionally with sonication, the cleaning agents are forced into the matrix of the implant using a series of "n" cycles of increased and decreased pressure. The matrix channels of the implant (including the interior of the soft tissue) are repeatedly filled and emptied of cleaning agent and components to be removed as a result of the oscillating pressure. The number of times this step is cycled may be from one to about 150 times (where n=1-150), alternatively from about 10 to about 50 times, alternatively from about 5 to about 20 times).

Preferably, the cleaning agent is made to perfuse the implant by use of cycling pressure in a sufficient number of cycles. The number of cycles may be from 1-150 times, preferably about 1-50 times, more preferably about 5-10 times. Suitable cyclically increased and decreased pressures are set forth above. Suitable temperatures at which the cleaning agent is contacted depend in part on the cleaning agent and its concentration, but desired temperatures include at least about 30° C., alternatively at least about 40° C., alternatively at least about 42° C., alternatively at least about 48° C. When the cleaning agent comprises a relatively high concentration of alcohol, it may be desirable to employ lower temperature, for example, about 35° C., about 30° C., about 25° C. or even lower. The cleaning agent (other than the oxidizing sterilant) can be contacted with the implant for a suitable time period, for example from about 1 minute to about 120 minutes, alternatively from about 5 minutes to about 20 minutes, alternatively about 10 minutes. The foregoing time periods may be consecutive minutes, or they may be partitioned or separated by time periods where the implant is contacted with other cleaning agents, rinsing fluids, or other solutions.

The implant may be machined or shaped or otherwise process (e.g., dimineralized) either before and/or after treatment with the foregoing cleaning agents. In many circumstances, this processing will be sufficient to passivate the implant, and the implant may be packaged. Alternatively, it may be desirable to load the implant into a reaction chamber, or allow tissue to remain in the reaction chamber, for additional treatment using the same or different steps and/or the same or different cleaning agents than those described above. A deep-penetrating cleaning, passivation or sterilization cycle, preferably under programmable logic control, is then conducted, optionally using different cleaning agents than cleaning agents B, C, D and E. For example, at this point, the cleaning agents may be one or more of the cleaning agents (and methods of using such cleaning agents) described in U.S. Pat. Nos. 6,482,584; 6,613,278; and 6,652,818. More particularly, one or more of the following cleaning agents may be contacted with the implant comprising the soft tissue: 6M urea or other chaotropic agents, e.g. 4 M guanidine HCl, to reduce implant antigenicity (cleaning agent F); 1% sodium hypochlorite, to inactivate viruses, bacteria, fungi or other residual contaminants (cleaning agent G); 1N sodium hydroxide, to inactivate viruses and bacteria (cleaning agent H); 6% hydrogen peroxide, as a sterilant (cleaning agent I); hexane, ether, diethanolamine (DEA), toluene, xylene, butane, CO2 (supercritical), isobutane, propane, acetone, isopropanol, methanol, ketones, ethers, aliphatic or aromatic hydrocarbons, HCl, gasseous HCl (cleaning agent J); and mixtures of F, G, H, I, J in any desirable proportions. Those skilled in the art will appreciate that different cleaning agents may be employed or that mixtures of the described cleaning agents may be possible.

Again, in accordance with the present techniques, before a cleaning agent comprising peroxide (such as cleaning agent I) is applied to the soft tissue, the soft tissue is tensioned or contacted with an alcohol. The soft tissue may be tensioned or contacted with an alcohol after a cleaning agent comprising a peroxide is applied to the tissue as well.

Suitable alcohols for use in the present processes include methanol, ethanol, propanol (including isopropanol), and butanol (including isobutanol and tert-butyl alcohol). Isopropanol is presently preferred. The alcohol may be provided in a solution or mixture, with preferred concentrations ranging from about 0.1% to about 100%, alternatively from about 5% to about 95%, alternatively from about 10% to about 80%. It is contemplated that the concentration of alcohol in an earlier contact step may be higher than the concentration in later contact steps. Preferred alcohols are those having low molecular weights (for example, in the range of from about 32 g/mole to about 360 g/mole, alternatively alcohols having molecular weights equal to or less than about 61 g/mole, alternatively about 90 g/mole, alternatively about 120 g/mole, alternatively about 240 g/mole, alternatively about 360 g/mole) and/or melting points below the operating conditions of the embodiment being used of the present processes. It is contemplated that other protective agents might be used in place of alcohols, for example polyols. Preferred polyols are those having relatively low molecular weights (for example, in the range of from about 32 g/mole to about 360 g/mole).

Oxidizing sterilants that may be used in the present processes include peroxides, oxides, hypochlorites, percarboxylic acids, and ozone. A preferred peroxide for use in the present processes is hydrogen peroxide. The oxidizing sterilant may be provided in a solution or mixture, with preferred concentration ranging from about 1% to about 10%, alternatively from about 2% to about 8%, alternatively from about 6% to about 7%. Preferably, an aqueous solution of hydrogen peroxide is provided having a concentration range of from about 1% to about 10%. Suitable exposure times and temperatures are mentioned above.

Suitable rinsing fluids for use after contacting the implant with the oxidizing sterilant include alcohols, polyols (for example, glycerol), acetone, saline solutions, water, and mixtures thereof. The rinsing fluid can be provided as an aqueous solution. Aqueous solutions containing monohydric alcohols having one to eight carbon atoms are presently preferred for use as the rinsing fluid.

Those skilled in the art will appreciate that the specifics of the processes outlined above may be modified, without departing from the present disclosure. Other cleaning agents, solutions or concentrations than those suggested herein may be used, the number of cycles between elevated and reduced pressure, the cycling times, pressurization and depressurization levels and periods may be altered, according to the requirements for a given implant tissue. Materials cleaned according to this procedure include, but are not limited to tissues such as: tendons, ligaments, fascia, whole joints, dura, skin, pericardia, heart valves, veins, neural tissue, submucosal tissue, (e.g. intestinal tissue), cartilage, mineralized, demineralized, or partially demineralized cortical bone, mineralized, demineralized, or partially demineralized cancellous bone, non-tissue materials such as metals, ceramics, and polymers, and assemblies, combinations, or mixtures comprising any of the foregoing materials.

Variants of the process employing alcohol as a protectant against damage from peroxide may be applied to treat thinner types of soft tissues, for example, cardiovascular tissue such as blood vessels and heart valves, pericardium, or dermis. Thinner tissue types may require reductions in contact times, pressures, and magnitude of kinematic restraint. Also the rates of pressure change, the type of kinematic restraint, and the type of concentrations of chemical agents may be adjusted.

Figure 2:
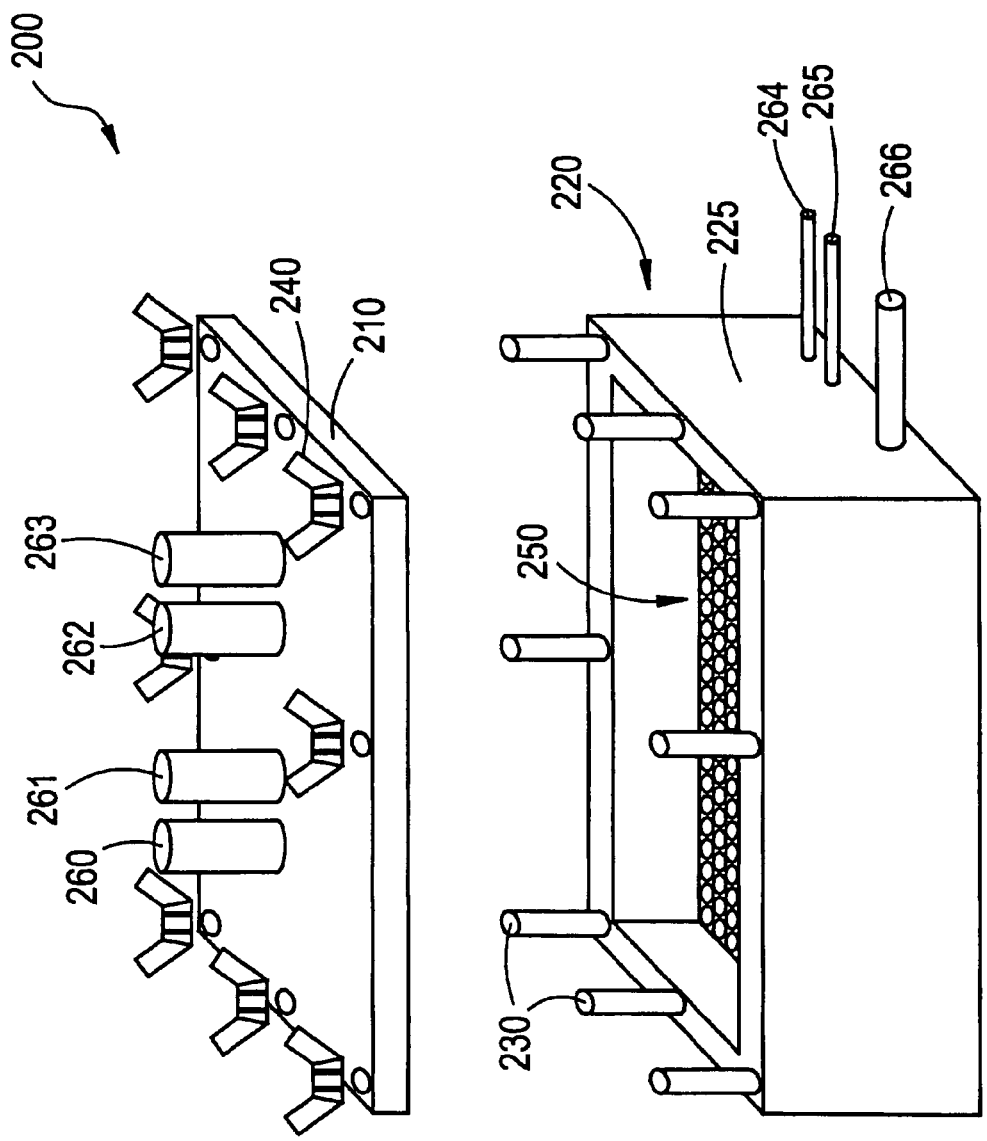
FIG. 2 shows a treatment chamber that may be used for the present processes.

The present processes will suggest to those skilled in the art a number of possible alternate processes to facilitate implant treatment as disclosed herein and devices to achieve the steps outlined above. Thus, for example, in one embodiment according to this invention, a device such as that shown schematically in FIG. 2 may be employed for semi-manual implementation of a cyclic perfusion passivation process using the present techniques. A chamber 200 comprising a lid 210 and a trough 220 is adapted for cyclic perfusion passivation of implants. A series of posts 230, onto which a series of bolts 240 may be tightened are provided for securing the lid 210 to the trough 220. A grating 250 is provided inside the chamber 200 for receiving implant material to be treated. Through the lid 210 is provided a series of access ports 260, 261, 262, 263. Access port 260 is a sterile water input line. Access port 261 is an input line for other fluids, such as solutions containing cleaning agents. Access port 262 is a vacuum line. Access port 263 is a line for pressure input. In addition, a port 264 is provided for insertion of a temperature probe. Port 265 is a port for supplying power to a sonicator built into the walls 225 of the chamber 200. Port 266 is a drain. Accordingly, a device such as that shown in FIG. 2 could be used carrying out a cyclic perfusion passivation process in which alcohol and peroxide are used to passivate an implant comprising a soft tissue.

Figure 3:
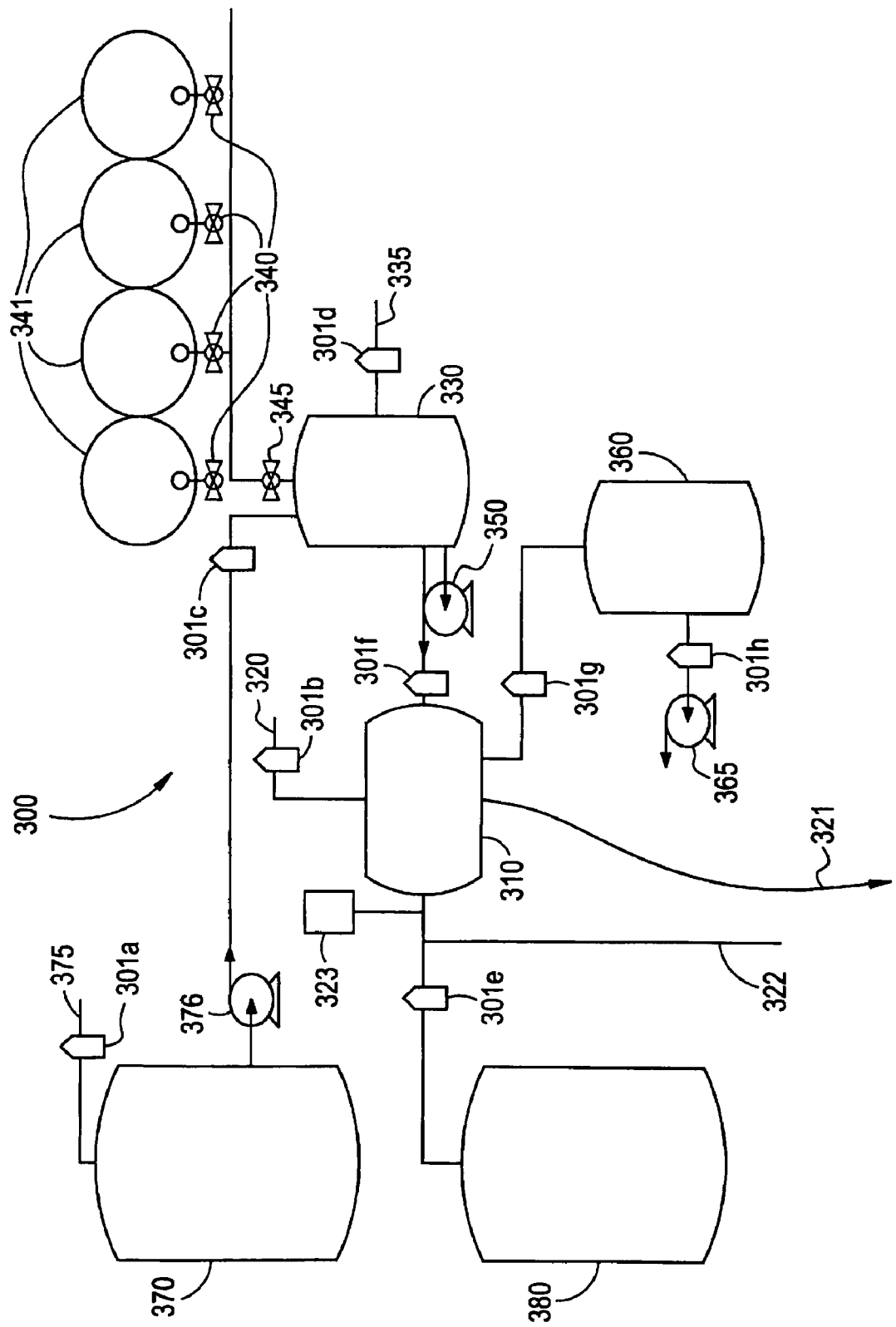
FIG. 3 shows an automated or semi-automated apparatus for conducting the present processes.

With reference to FIG. 3, an automated or semi-automated apparatus 300 may be used for carrying out a treatment process. Per this disclosure, programmable logic controllers activate or deactivate valves or solenoids 301a-h at predetermined times in the cleaning cycle. An implant is placed in a reaction chamber 310 which is sealed. An atmospheric vent 320 is provided to permit entrance and removal of filtered air, and a drain 321 is provided to remove waste or solvents. Cleaning agents (for example, an alcohol solution or a peroxide solution) are introduced into reaction chamber 310 from a chemical mixing tank 330 which has a filtered vent to atmosphere 335, to avoid formation of a vacuum in the tank 330. Chemical feed lines 340 lead from fluid reservoirs 341 to the chemical mixing tank 330 via a common conduit 345. A programmably controlled pump 350 is operated to pump appropriately mixed fluids from the tank 330 into the reaction vessel 310. Vacuum or negative pressure is applied to the reaction vessel 310 by means of a vacuum receiver tank 360, in which a source of negative pressure is created by vacuum pump 365. The inclusion of a vacuum reservoir 360 is desirable so that essentially instantaneous vacuum of known dimensions may be applied to the reaction chamber 310, without the need for a vacuum pump such as 365 having to gradually develop the negative pressure. Vacuum receiver tank 360 may be evacuated by pump 365 while reaction tank 310 is under positive pressure. A source of sterile water, physiological saline, or like aqueous solution is provided in storage tank 370, which has a filtered vent 375 to prevent formation of a vacuum in tank 370. Pump 376 provides for rapid infusion of aqueous solution into chemical mixing tank 330 for introduction into the reaction chamber 310. Those skilled in the art will appreciate that the water from tank 370 may also be directly introduced into reaction tank 310, without having to first be introduced into chemical mixing tank 330. Positive pressure is stored in pressure tank 380 which is pressurized by a compressor of filtered gas, to retain sterility in the reaction tank 310. In practice, an appropriately programmed computer or programmable logic controllers permit venting of the reaction chamber 310, to permit loading of tissue. The chamber is then sealed and fluid is introduced and removed, as outlined above, to complete the implant cleaning process. In addition, a source of filtered sterile steam 322 to rapidly sterilize the internal, filtered and sterile zone of the device is provided. It is also desirable to include a heat exchange means 323 to rapidly equilibrate the system temperature. Water cooled, air cooled, nitrogen cooled, water heated, thermocouple heated or like radiative means are all acceptable, depending on the internal temperatures desired.

Subsequent to penetrating passivation of the implant materials, the implant materials may be placed in their final packing. Preferably, this is achieved in a sterile environment to avoid introduction of any adventitious bioburden. To ensure sterile packaging, with the final machined grafts in their final, unsealed packages, the implants are exposed to a vapor-phase hydrogen peroxide/peracetic acid or like vapor-phase sterilizing environment. The packages are then closed to ensure that no contamination may occur upon removal of the implants from the sterile field for storage or shipment to surgeons. The sealed packages may then, optionally, be subjected to levels of gamma or other types of irradiation known to not adversely affect tissue properties (e.g. below about 3.0 Mrad, or for short periods of time to effect surface sterilization, and to ensure internal destruction of any residual large-genome organisms; however, such internal treatment is generally not required, deep sterilization having been achieved according to the cleaning protocol, or a variant thereof, as described herein). Other surface and redundant internal sterilization methods, including exposure to electron beams, exposure to ethylene oxide, and the like, may also be conducted at this stage, so long as toxicity or diminishment of desirable biological activities is not thereby effected.

As a further enhancement to the process defined herein is the ability to produce implant materials with perfusion of desirable bioactivities. Accordingly, in rinse steps after contact with cleaning agents, a solution or mixture containing desired antibiotics, anti-inflammatory drugs or other biologically active agents may be employed to infuse antibiotic or other desired bioactive substances into the cleaned, passivated tissues. Alternatively or in addition, growth factors, such as bone morphogenetic proteins, cartilage derived growth factors, tissue growth factors, natural (autograft, allograft or xenograft) or recombinant, and the like known in the art may be perfused into the implant. In one preferred embodiment, a solution containing expressible nucleic acids in plasmid, viral or linear DNA or RNA vector form is infused into the implant. The nucleic acid preferably encodes an appropriate growth factor (for example, BMP, TGF-$\beta$, CDMP, VEGF, IGF, FGF, or any other known growth factor), antineoplastic agent, peptide or protein (P15), depending on the nature of the tissue. The nucleic acid may be DNA, RNA or it may be combinations thereof, optionally including synthetic nucleotides or markers to track nucleic acid penetration and concentration. In addition, by finely grinding demineralized bone matrix (DBM) and forming a hydrated slurry or aqueous mixture thereof, implants may be perfused with the DBM which contains a complex mixture of growth factors. Alternatively, using the present techniques, a bone implant may be partially demineralized to expose growth factors prior to implantation. Similarly, bone marrow or bone marrow extracts may likewise be perfused into the matrix of an appropriate implant. Alternatively or in addition, antibiotics, cancer treatments, and, "genes containing sequences for restorative or therapeutic modalities may be perfused into the implant.

In a further embodiment of the present techniques, a cleaning process is applied to rid a tissue of a pathogenic organism or condition. This can be achieved, for example, by harvesting a diseased mandible or any other bone or tissue, ravaged by cancerous cell growth. The section of autograft is cleaned and passivated ex vivo, perfused with growth factors, nucleic acids encoding growth factors, antibiotics, antineoplastics, antiinflammatories analgesics or any after desired biologically active substance, and then re-implanted into the same or a different patient, to provide a non-pathogenic tissue.

As can be appreciated from the foregoing detailed disclosure, the present processes may be carried out at any stage of implant production, and do not require special preparations such as removal of cartilage, or potentially implant damaging steps such as drilling of holes. The present processes may be readily incorporated into an automated, controlled, or validated tissue processing protocol Accordingly, the present processes lends themselves to enhanced quality control, inventory control and efficiency.

As an added advantage, in one embodiment, a cleaning process efficiently removes, dilutes or denatures endogenous enzymes which otherwise might result in degradation or autolysis of bone matrix or tissue matrix. This is achieved by, for example, cyclically exposing the tissue to detergents, reducing agents (for example, dithiothreitol, DTT, and the like known in the art for disruption of protein disulfide bonds), peroxide, isopropanol and the like as disclosed herein. As a result of the removal, dilution or destruction of the endogenous enzymatic activity, the need to freeze or freeze-dry the implant is reduced or eliminated, providing a significant advantage. It is difficult to maintain implant tissues in a frozen state and it is slow and expensive to have to lyophilize (freeze-dry) tissue implants, including allograft, autograft or xenograft bone implants. By treating such tissues according to the present processes, and then storing the tissues in a sterile environment or packaging, the cost and time delays inherent in freezing and freeze-drying of tissues is eliminated.

As an additional aspect of the present invention, processes and apparatus are provided for applying kinematic restraint (including tension, compression or immobilization) to an implant, particularly to an implant comprising a soft tissue such as a tendon. It has been found that when implants comprising soft tissues, such as tendons, bone-tendon-bone grafts, and other soft tissues, are subjected to a treatment process (for example, cleaning, passivation, and/or sterilization that includes contact with one or more cleaning agents, damage to the implant (especially damage to soft tissue) can be reduced by applying tension to the implant (particularly the soft tissues) during at least some portion(s) of the treatment process. By applying a kinematic restraint, such as tension, to soft tissue, damage caused by the treatment process (or one or more of its individual steps) may be reduced, minimized or eliminated. Furthermore, applying tension to the soft tissue can improve the effectiveness and/or consistency of the treatment process.

Conventional processing methods for bone and soft tissue implants include those described, for example, in U.S. Pat. Nos. 5,333,626; 5,512,662; 5,556,428; 5,769,893; 5,797,871; 5,976,104; 6,024,735; 6,293,970; as well as other patents and publications. In conventional processes, an implant comprising soft tissue has been subjected to treatment chamber without tensioning of the implant or kinematic restraint of the implant. In such conventional processes, the positioning and orientation of the soft tissue in the process may be altered by cleaning agents, implements or methods used in the processes. This altered positioning or orientation may lead to inconsistencies between different implant specimens, as different implant specimens may have different exposures to the cleaning agents (for example, as a result of overlapping tissues or tissues wrapped around themselves). Also, inconsistent cleaning and access of the cleaning agents to a single tissue may result because one area of the tissue may be overexposed because it is on the outside, and another area of the tissue is balled up, trapped or improperly constrained on the inside receives less exposure to the cleaning agents. Another problem that may arise from the use of conventional sterilization processes with soft tissues, is that the soft tissue may shrivel, leading to an undesirable appearance and structural changes which can later cause excessive post surgical laxity. Yet another concern in the treatment of soft tissues is inflammation. Tissue inflammation may be caused by the interaction of various cleaning agents with blood, fats, or other material inside the soft tissue. For example, the reaction of peroxide with endogenous materials can cause swelling of the tissue and lead to tissue damage. These reactions are commonly referred to as a foaming reaction, as observed in the topical application of peroxide to a surface wound. Remaining byproducts of the peroxide reactions may eventually lead to post surgical inflammatory response. When the tissue is not stretched out (if it is unrestrained during treatment), the foaming reaction may cause more harm, since the foam and byproducts are more likely to be caught inside the tissue.

The present processes and apparatus may reduce, minimize or eliminate one or more of the foregoing problems. By applying tension to an implant comprising a soft tissue during a treatment process employing cleaning agents, the positioning of the soft tissue in the chamber can be maintained in a desired fashion, and the cleaning agents are unlikely to be applied with enough force to change the positioning. Because cleaning agents contact the implants (particularly the soft tissue) more uniformly and predictably, there will be more consistency between different implants and within a single implant. Soft tissues will have less tendency to shrivel, and as a result there will be less likelihood of generating implants having undesirable appearance. By applying tension to a soft tissue during a treatment process, inflammation and damage from internal foaming reactions can be reduced, because there is greater opportunity for the foaming action to exit the stretched tissue, rather than remain inside the tissue to cause more damage. Additionally, the tension applied during processing will protect the graft from post surgical laxity which can be caused by shrinkage and shriveling of the graft during conventional processing.

It is desirable to provide an apparatus for applying kinematic restraint that has few parts, is easy to use, and can withstand the chemicals and conditions it will encounter. It is undesirable for the apparatus to have an excessive number of restraints or parts to be actuated. Furthermore, the apparatus should be made from a material that is able to withstand the environments of use and cleaning. For example, it is desirable for the apparatus to be capable of withstanding temperatures in an autoclave which has temperatures in the area of about 120° C. (about 250° F.). In the autoclave, steam should contact and sterilize the various parts of the apparatus. Accordingly, if the apparatus has lots of pieces, screws, tight corners, or little features, it will be less certain that the autoclave will adequately sterilize all those parts of the apparatus, so that it can be used again.

The apparatus for applying kinematic restraint should be designed to expose most or substantially all of the tissue to cleaning agents used in a treatment process. It is generally undesirable for the apparatus to cover significant amounts of the tissue, or restrict the flow of cleaning or rinsing solutions during a treatment process.

It is contemplated that the apparatus may find use with implants that comprise soft tissue by itself and with implants comprising soft tissue and bone (or other relatively hard material). Processes and apparatus are provided for applying tension or other kinematic restraint to soft tissue alone, such as a tendon or ligament, and to implants comprising soft tissue and bone, such as bone-tendon-bone implants, which have bone blocks on the ends of a tendon. In view of the variety of implants suitable for use in the present processes and apparatus, various embodiments of the apparatus are contemplated and described herein. The various embodiments may differ in the ways that the implants are fastened to the apparatus and/or the ways that kinematic restraint is applied, but the embodiments share a common use in applying kinematic restraint to an implant comprising a soft tissue, thereby improving a treatment process on that implant.

A suitable apparatus for applying kinematic restraint includes fasteners adapted to securely hold one or more portions of an implant, and an adjustable spacing member disposed between the two fasteners. The fastener can be any device suitable for fastening a hard or soft end of the implant, such as a block, clip, hook, pin, loop, bracket, ratchet, or a combination of any of those means. The fastener itself may include clips that hold the implant to the fastener, or the fastener may be used in connection with other devices, such as zip ties. In the embodiments set forth below, zip ties are examples of the means that can be used to hold the ends of the implant. Because the naturally occurring attachments within the implant (for example, the attachments between the tendon and the bone blocks) have been preserved, one can zip tie the bone blocks, and that will hold the entire implant in place. The zip ties may be applied by a zip tie gun that is commercially available. Zip tie guns can be used so that a certain load is applied and then released and the end of the zip tie is snipped off. The fastener can be made from a material selected from the group consisting of plastics, metals, ceramics, composites, and combinations thereof.

Preferably the spacing member is a resilient member and can be selected from the group consisting of springs, racks, levers, linkages, flexible or rigid plastic members, and unitary or multipart members. Alternatively, the spacing member can be a shaft on which the fasteners are disposed.

The apparatus is not only useful during processes for cleaning, passivation, and/or sterilizing an implant, but also may be useful and adapted to provide kinematic restraint to the implant throughout one or more steps of recovery, processing, packaging, shipment, storage, preoperative preparation of the implant, interoperative preparation of the implant, and interoperative handling of the implant.

When the apparatus is used to apply tension to an implant comprising a soft tissue, the amount of tension applied to a tendon is desirably between about 3 and about 5 pounds of force (between about 13 and about 22 Newtons), alternatively from about 1 to about 10 pounds of force (between about 4.5 and about 45 Newtons), alternatively from about 0.5 to about 20 pounds of force (between about 2 and about 89 Newtons). Accordingly the tissue tensioner should be designed to apply an amount of tension in one or more of the foregoing ranges.

The materials used for the tissue tensioner should be strong, biologically inert (in other words, they do not interact with biological tissues) and able to withstand the contemplated chemical and temperature environments for their use and cleaning. Suitable materials for the tissue tensioner include (but are not limited to) polymers, ceramics, and non-corroding metals. Preferred metals include stainless steel, titanium, and alloys such as nickel-based alloys, or materials obtained by plating steel with copper, nickel, chromium. In one preferred embodiment, the shaft, thumb screw, spring and wing nut are made from stainless steel, and the fasteners and end piece are made from DELRIN plastic, which is a high temperature plastic that is sufficiently hard for the contemplated uses. DELRIN also has suitable tensile strength and temperature resistance, and it is biologically inert. In another preferred embodiment, all parts of the tensioner are made from an suitable inexpensive, sterilizable material, such as stainless steel, or other common sheet metals, or plastics, so that the tensioner might accompany the graft throughout one or more of the steps of processing, packaging, shipment, storage, and preoperative preparation.

Figure 4:
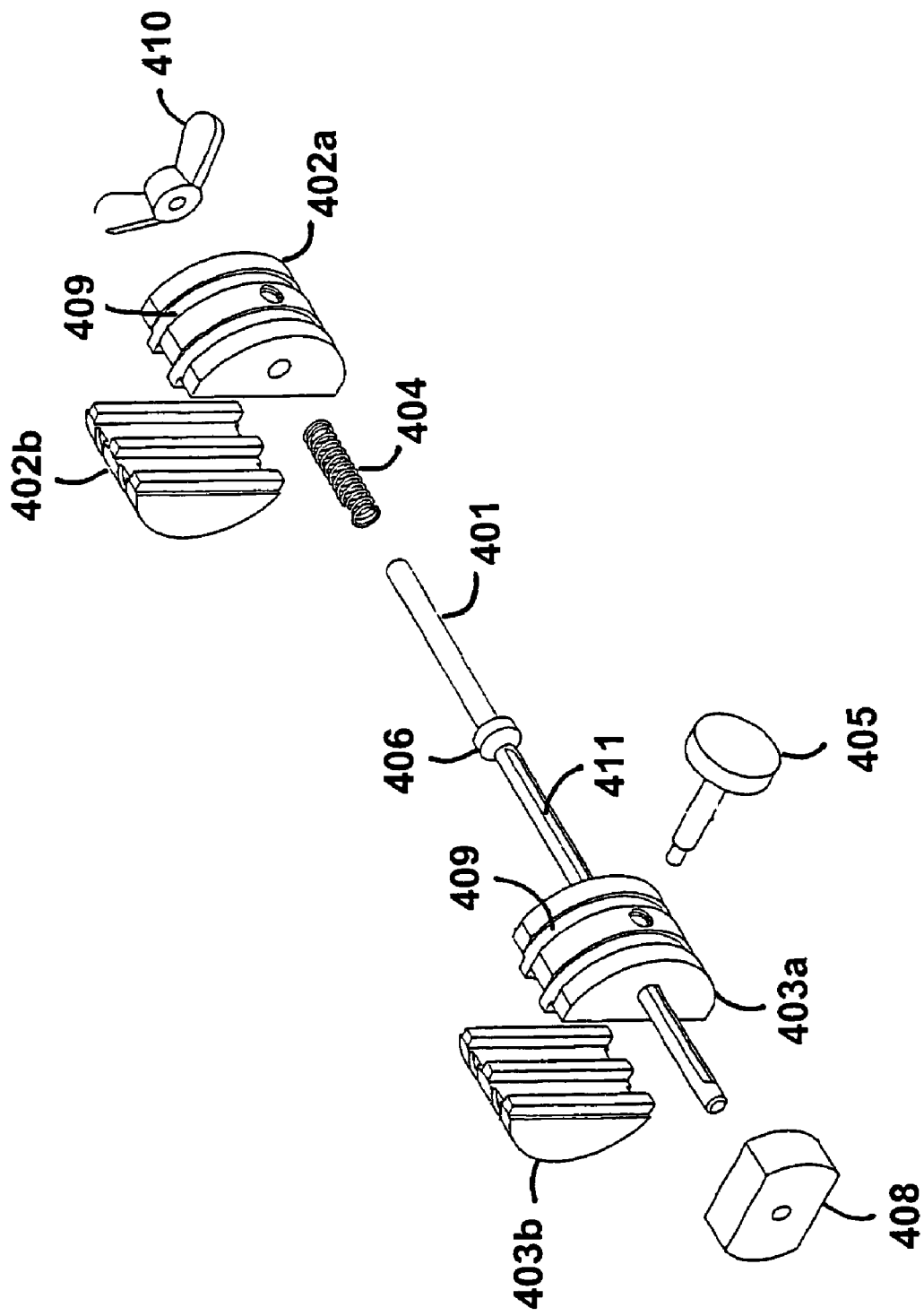
FIG. 4 shows a tissue tensioner designed for an implant comprising a tendon that does not have any bone attached.

As an example of an apparatus for applying kinematic restraint, tissue tensioners are described which apply tension to an implant comprising a soft tissue. FIG. 4 shows a tensioner designed for an implant comprising a tendon that does not have any bone attached. Thus, the two ends of the implant (which merely may be the ends of the portion of the implant to which tension is to be applied) are soft tissue. Accordingly, this tissue tensioner includes a shaft 401 having two fasteners 402 and 403, and each of the two fasteners has two separate fastener halves 402a, 402b, 403a and 403b. The fastener halves are preferably made from DELRIN plastic or other suitable polymeric material. The ends of the implant are placed between the two fastener halves 402a, 402b, 403a and 403b, and a suitable fastening mechanism is used to firmly hold the ends between the two fastener halves. For example, zip ties may be wrapped around the fastener halves in their grooves 409 and tie the halves together. The two fastener halves clamp down on the tissue and firmly hold the tissue. Fastener halves 402a, 402b, 403a and 403b have teeth which interlock but also allow cleaning agent to travel between the teeth to contact the ends of the implant.

A spring 404 is disposed along the shaft 401. After the ends of the implant are fastened to fasteners 402 and 403, an operator would pull on fastener 403. Fastener 403 is adapted to receive a thumbscrew 405 (a screw with a tall head and a shaft, intended to be tightened and loosened by hand). As fastener 403 is pulled away from fastener 402, spring 404 is depressed on the other side because the other fastener 402 is pulled along by the tissue. Spring 404 is compressed on one side by the stop 406 in the middle of the shaft 401, and on the other side by fastener 402. When an operator pulls on the fastener 403, the tissue tensioner transmits force through the tendon and pulls on the other fastener 402 and that compresses the spring 404. The force of the spring is being countered by the tension in the tendon. The thumb screw 405 can then lock it in place once the tissue is stretched to the desired tension. When a desired tension is reached, due to the spring being compressed, the operator would lock the tensioner by turning the thumb screw 405 so that it engages channel 411 on the shaft 401, thereby holding fastener 403 in the tensioned position. Once the thumb screw 405 is on, fastener 403 will not stretch any further or retracted to a less-tensioned position.

The tissue tensioner shown in FIG. 4 includes an end cap 408 on the far left of the figure and a wing nut 410 on the right. The end cap 408 and wing nut 410 do not act in providing tension to the tissue and are present for the operator's convenience in using the tissue tensioner.

End cap 408 is provided so that the end of the shaft is not exposed and fastener 403 will not fall off the shaft 401 when the tensioner is not in use. Wing nut 410 is provided as a back-stop for fastener 402, so that it is not pushed off the shaft 401.

Fastener 402 (which is in contact with the spring 404) is forced by the spring 404 against the wing nut 410 initially (before the tissue tensioner is put into use). Fastener 403 (which has the thumb screw 405 in it) will move back-and-forth freely along the shaft when the thumb screw 405 is not engaged. Resistance to movement by fastener 403 along the shaft should be minimal to facilitate movement with the tissue in place.

When the implant is fastened in place on the two fasteners 402 and 403, the tensioner is zeroed at that point. Then the operator pulls fastener 403 until a desired compression on the spring is achieved, which means a desired tension is being applied to the implant. At that point, the thumb screw 405 is set in place to hold fastener 403 in position and maintained the desired tension. The tissue tensioner with the implant in place is then ready to be subjected to a sterilization process. For example, the tissue tensioner and implant can be placed in the treatment chamber shown in FIG. 2 or FIG. 3 for treatment as described above.

Shaft 401 should be long enough to accommodate the intended range of acceptable tensioning of implants. The length is such that it can accommodate the expected range, or allowable range, of implant sizes. The shaft should be long enough that there is still some room left over if one stretches out the longest tendon that is going to be processed, and it should be short enough that it is not bottomed out when the shortest tendon that will be processed is attached.

Figure 5:
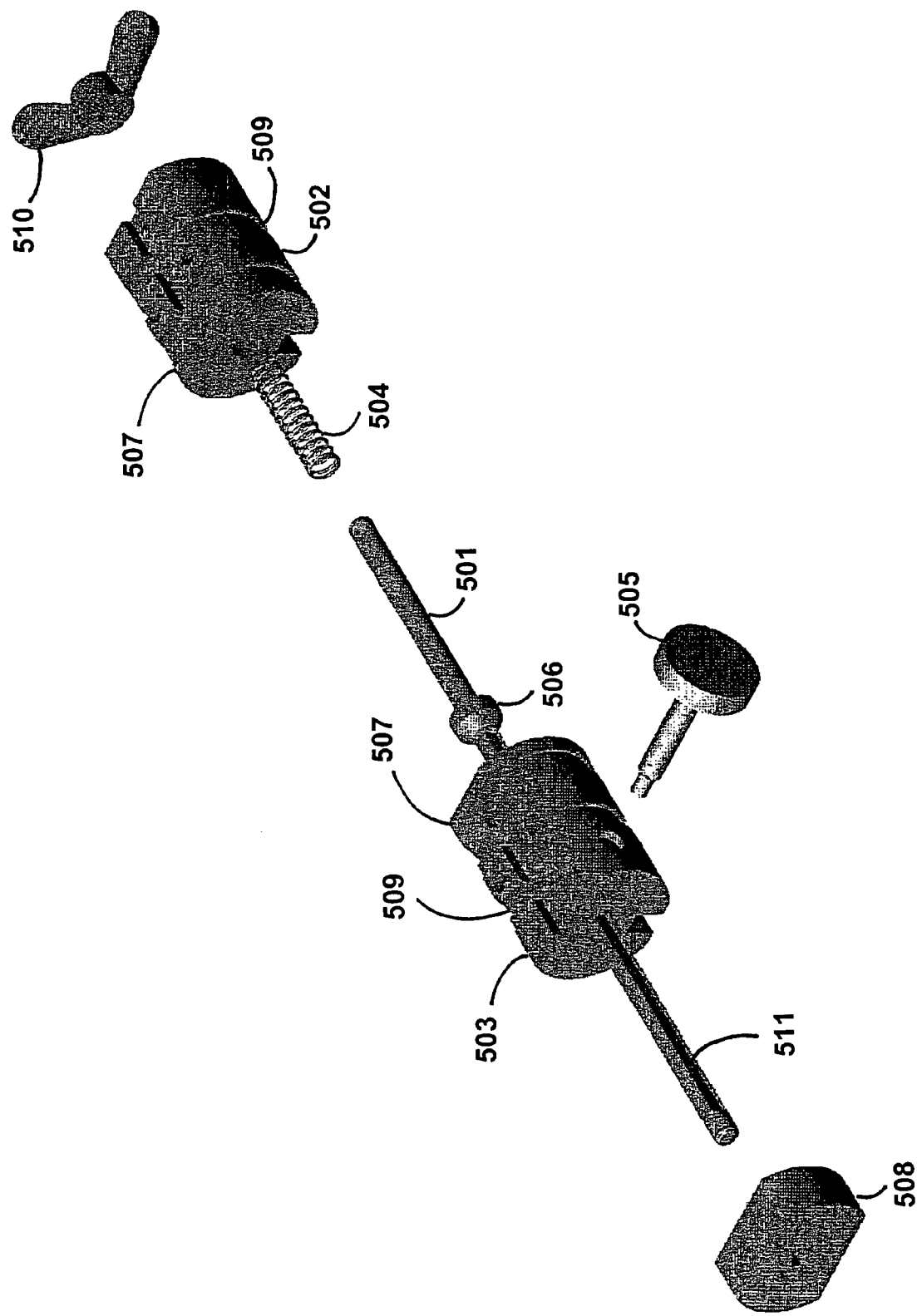
FIG. 5 shows a tissue tensioner designed for an implant comprising bone blocks at either end.

FIG. 5 shows a tensioner designed for a bone-tendon-bone graft (or implant which has bone or hard material at either end). The tensioner comprises a shaft 501 and two fasteners 502 and 503. It has a relatively small shaft (as compared, for example, to a tensioner designed for an Achilles tendon), since the tendon employed is a relatively short tendon. The spring 504 is disposed along the shaft 501. The bone blocks of the implant are going to set or rest on the fasteners 502 and 503, which are different from fasteners 402 and 403 due to the differences in the ends of the implants. For the tissue tensioner of FIG. 5, it is contemplated that bone blocks or other or hard material will be attached to the fasteners 502 and 503, rather than the soft tissue attached to the fasteners in the tissue tensioner of FIG. 4. The bone blocks are fastened to fasteners 502 and 503 by a suitable fastening mechanism, such as zip ties that fit in the groves 509 that go around the entire fastener, effectively tying the bone blocks to the fasteners 502 and 503.

The surfaces of the fasteners 502 and 503 are flat, but they have canals to allow the cleaning agents to get underneath the portion of the implant that is in contact with the fastener. There is a ledge or lip 507 toward the middle of the tensioner that is adapted to contact the bone block so that it does not slip off the fastener.

The spring 504 is disposed along the shaft 501. An operator pulls on fastener 503, and spring 504 is compressed as the other fastener 502 is pulled along by the tissue. After the tissue is secured, when an operator pulls on the fastener 503, the tissue tensioner transmits force through the tendon and pulls on the other fastener 502 and that compresses the spring 504. The force of the spring is being countered by the tension in the tendon. The thumb screw 505 can then lock it in place once the tissue is stretched to the desired tension. The thumb screw 505 is then screwed down and engages the channel 511 in the shaft 501.

Once a sufficient tension is reached, and the spring is sufficiently compressed, the operator would lock the tensioner by turning the thumb screw 505. Once the thumb screw 505 is engaged, the fastener should not move in either direction.

The tensioner includes a thumb screw 505, a shaft 501, an end-cap 508 on the far left, a fasteners 502 and 503, wing nut 510, the spring 504 over the shaft 501, and stop 506 in the middle of the shaft 501, all of which operate as described in connection with the same apparatus in FIG. 4.

The tissue tensioner with the implant in place is then ready to be subjected to a sterilization process. For example, the tissue tensioner and implant can be placed in the treatment chamber shown in FIG. 2 or FIG. 3 for treatment as described above.

Shaft 501 should be long enough to accommodate the full range of acceptable tensioning of grafts. The length is such that it can accommodate the expected range, or allowable range, of graft sizes. The shaft should be long enough that there is still some room left over if one stretches out the longest tendon that is going to be processed, and it should be short enough that it is not bottomed out when the shortest tendon that will ever be processed is attached.

The fasteners 502 and 503 are held on the shaft and the bone blocks are held on the fasteners. The fasteners are preferably made from DELRIN plastic or other suitable polymeric material. The fasteners are captured by the shaft and they slide back-and-forth on the shaft. The bone blocks are attached to them by resting on the primarily flat surface, which are facing up in FIG. 5. The bone block is placed on that flat surface and then two zip ties are wrapped completely and firmly around the fasteners and the bone block both.

The tissue tensioner can include a visual indicator to indicate the level of tension being applied by the tensioner. For example, in the context of FIG. 5, when the operator pulls on fastener 503, when it reaches approximately the recommended point for tension, fastener 502 passes over the end of the spring, and that point where the spring disappears from view is a visual indicator that the recommended level of tension (the recommended compression of spring 504) is achieved.

More broadly, the visual indicator can be as simple as a marking on the shaft or it may be a mechanical feature designed into the tensioner. The visual indicator may comprise a scale marked on the shaft. Alternatively, the visual indicator may comprise a stepped hole on fastener 502 and a spring 504 that passes inside the hole. The spring goes into the stepped hole a certain amount and then it contacts a step somewhere in the middle. The step is formed by a transition to a smaller diameter hole inside the fastener 502 on the side nearest the wing nut 510. The diameter of this hole is small enough so that a solid portion of the fastener 502 engages the spring 504, but large enough for the shaft 501 to pass through. At a desired point in the compression range of the spring, the end of fastener 502 reaches the lip 507 on the shaft, such that one cannot see the spring 504 anymore (it is hidden by fastener 502). If one compresses the spring, eventually the whole spring is inside the fastener. That serves as the visual indicator, that a proper amount of compression has been achieved. That provides a clear visual indicator that one has reached the right point. If the spring is no longer visible, there is sufficient tension. If one still sees spring, there is not quite enough tension.

The visual indicator can accommodate grafts of different lengths because when the implant is first laid in place, the tensioner is zeroed and self-aligning as fastener 502 is moved while placing the implant in place. So, the zero point with zero compression on the spring, is going to be where the implant is first pulled to its untensioned length. Regardless of tension length, the same tension or force is applied by the same degree of movement (i.e., compression) of the spring. By selecting a spring of appropriate length or force, one can provide a tensioner that gives a level of tension that is easily determinable and/or controllable.

Figure 6:
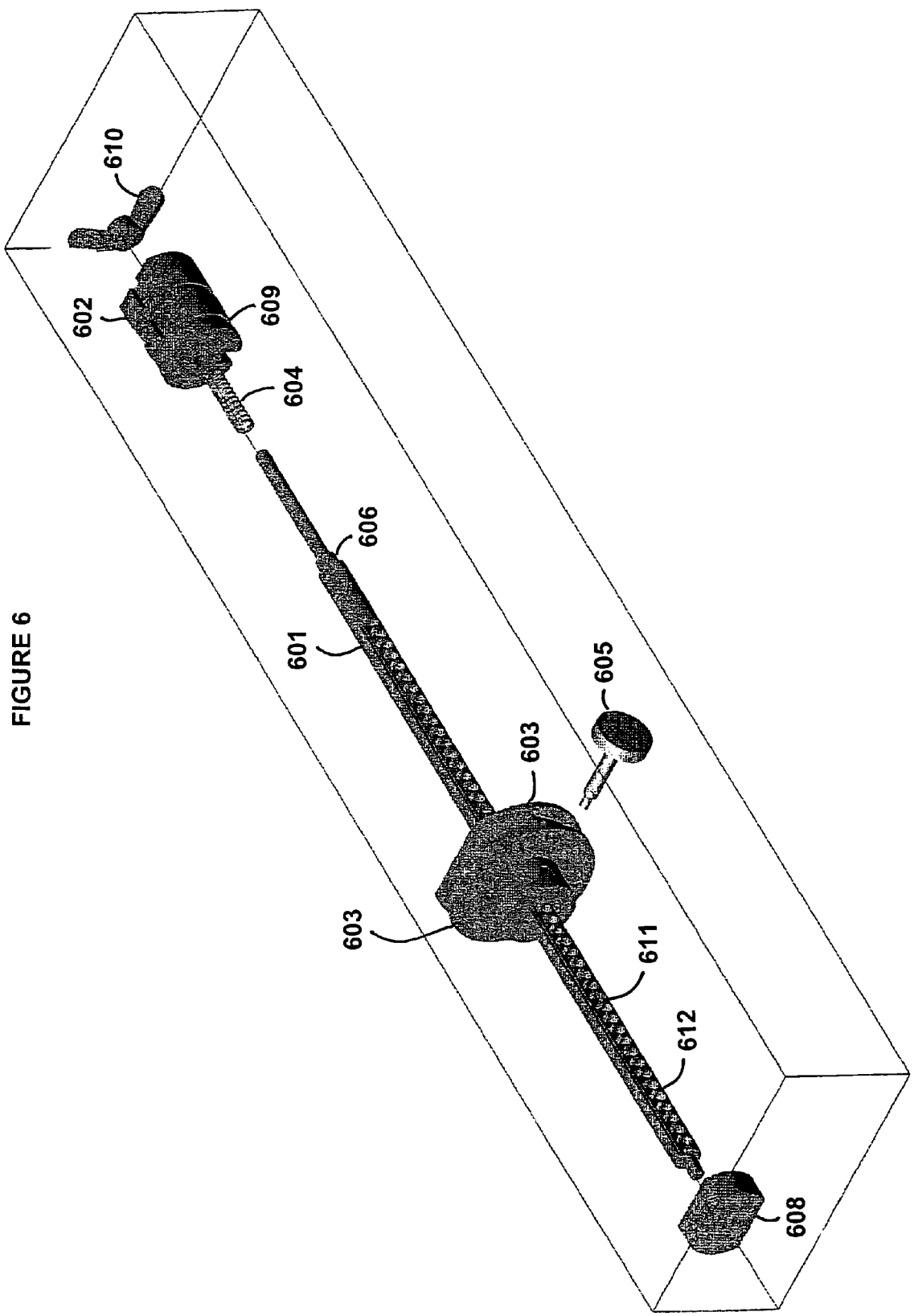
FIG. 6 shows a tissue tensioner designed for an implant comprising an Achilles tendon.

Though the visual indicator is described in the context of FIG. 5, it is applicable to the apparatus shown in FIGS. 4 and 6 as well as other apparatus.

FIG. 6 shows a tensioner designed for an Achilles tendon. It has a relatively long shaft 601, compared to the tissue tensioners of FIGS. 6 and 7, since the Achilles tendon is a relatively long tendon. In the Achilles tendon tensioner, fastener 602 is the same as on the tissue tensioner designed for a BTB graft (FIG. 5), since it is expected that the lower part of the Achilles tendon graft will include a bone block. Alternatively, this fastener can be in the form of the fasteners shown in FIG. 4, which is the tissue tensioner designed to hold graft ends comprising soft tissue. In FIG. 6, fastener 602 is used to strap down the bone block of an Achilles tendon graft. The tissue tensioner has a spring 604, thumbscrew 605, stop 606, ledge 607, end cap 608, grooves 609, and wing nut 610 which function in the same fashion as the same apparatus described in connection with FIGS. 6 and 7. The fasteners are preferably made from DELRIN plastic or other suitable polymeric material.

Fastener 603 has a different design which reflects the shape and structure of the Achilles tendon and implants comprising Achilles tendons. The Achilles tendon is rather thin and cord-like near the foot, but as it goes up the calf muscle, the Achilles tendon widens and fans out fairly dramatically. The Achilles tendon is about 2 or 3 inches across by the time it reaches the calf muscle and it wraps around the calf muscle. An implant comprising an Achilles tendon typically starts with the tendon at the heel bone, and a bone block is typically cut out off the heel bone to go along with the tendon as part of the implant. The implant typically comprises all of the tendon up to the calf muscle, and thus includes the wider portion of tendon that wraps around the calf muscle.

Fastener 603 has a generally round shape so that the operator can wrap the upper, wider portion of the Achilles tendon around this fastener 603. As a result, the shape and width of the portion of the tendon that fans out is maintained by fastener 603. Fastener 603 is grooved so that, like in the other tensioners, the operator can fasten the tendon to it (for example, by zip ties) and the tendon would fall between the inside and outside ledges. Fastener 603 has a relatively high wall, a low spot and another high wall, and a zip tie can go between the two high walls and clamp the tendon in place. Fastener 603 also has holes so that the cleaning agents can reach underneath the tendon that is fastened to the fastener, which helps profusion of the cleaning agents into the tissue.

The special fastener 603 designed for the Achilles tendon tensioner is exemplary of other fasteners which may be designed for other specific implant shapes and sizes. One of ordinary skill will recognize based on the present disclosure that other fasteners based on particular implants may also be provided and therefore fall within the scope of the present disclosure.

Figure 7:
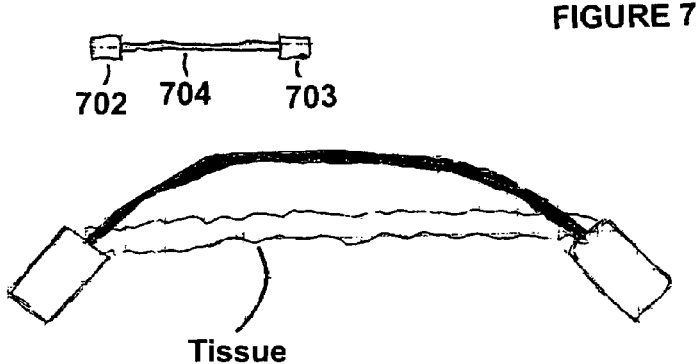
FIG. 7 shows a tissue tensioner comprising a leaf spring.

FIG. 6 also shows other features which are not limited to an Achilles tensioner, but rather are applicable to any of the tissue tensioners described herein. This figure shows a shaft 601 having a channel 611 which includes teeth 612 to engage the thumb screw 605. By virtue of the thumb screw engaging the teeth, that the fastener will stay where the operator places it and not move along the shaft. However, it has been found that these teeth 612 are not a necessary feature, and the tissue tensioners of FIGS. 6 and 7 are operative without teeth 612. The metal-to-metal contact of the thumb screw on a flat surface has been found to be sufficient to maintain the thumbscrew and fastener in place. FIG. 6 also shows a D-shaft, which will prevent the fastener from rotating around the shaft. Fastener 603 also has a D-shaped hole in its center so that there is no rotation of the fastener (and the tendon). The shaft can have any radially asymmetric cross section, such as a D-shape, a polygon shape, a round shaft with a key way cut into it. The fastener will have a reciprocally shaped hole to engage the non-radially symmetric shaft. Alternatively, the interior or exterior of the shaft could include ridges or individual steps where the thumb screw would tighten into a specific gap to give a better, positive lock and better fixation. Alternatively, the internal channel 611 of the shaft 601 could be a textured surface that provides additional friction with the thumbscrew 605 to hold it in place.

Alternate embodiments for the tensioner are also contemplated. FIG. 7 shows a tissue tensioner embodiment that employs a leaf spring 704 which is basically a flat piece of metal. When the leaf spring 704 is bent, it seeks to return to its original shape, thereby creates a force. To use this tensioner, the operator first has to bend it, then attach the bone blocks (or ends of the implant) directly to the ends of that leaf spring (or to fasteners 902 and 903 which are optionally attached to leaf spring), and then release the tensioner (stop bending it) so that tension is then applied to the implant by the tissue tensioner. This embodiment is similar to a bow in having a tendency to return its original shape, and the use of this tendency to create a useful force. The design is simple, but it requires more than two hands to place the implant on it. The design has a low part count and simplified geometric features. However, this tensioner would probably require multiple sizes to match up with the size ranges of implants. Also, the operator would be required to select the proper size of tensioner (for a given implant). There is also a risk of the tensioner springing back to the original position while the operator is trying to load it. It is contemplated that some type of fixture could be provided for holding this tensioner in the bent position while the implant is loaded onto it.

Figure 8:
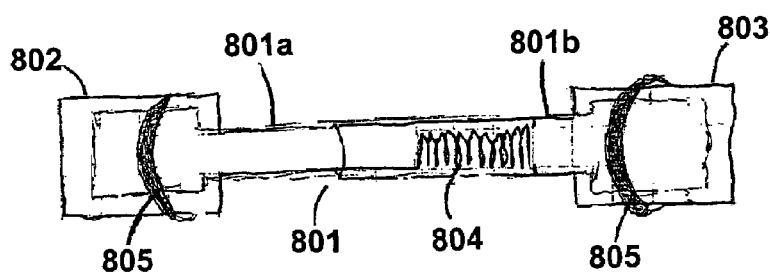
FIG. 8 shows a tissue tensioner comprising a telescope shaft.

FIG. 8 shows another alternative embodiment of a tissue tensioner. The shaft 801 is in two parts, 801a and 801b, and one part telescopes into the other. One part 801b is hollow, it has a gap that the other one 801a would fit through. The spring 804 is inside the hollow portion of 801b so that when the two parts of the shaft are pushed together, the spring is compressed. When the spring is compressed to a desired degree, and a desired amount of tension is created, the implant is attached to the fasteners 802 and 803 by bands 805, ties or another suitable fastening mechanism. When the operator stops pushing the two parts of the shaft together, the tissue tensioner would put the tension on the implant. Like the embodiment of FIG. 7, the tensioner must be compressed (the tension is created) before the implant is completely attached to the tissue tensioner. FIG. 8 demonstrates that the fasteners 802 and 803 can be integral with the shaft 801.

Figure 9:
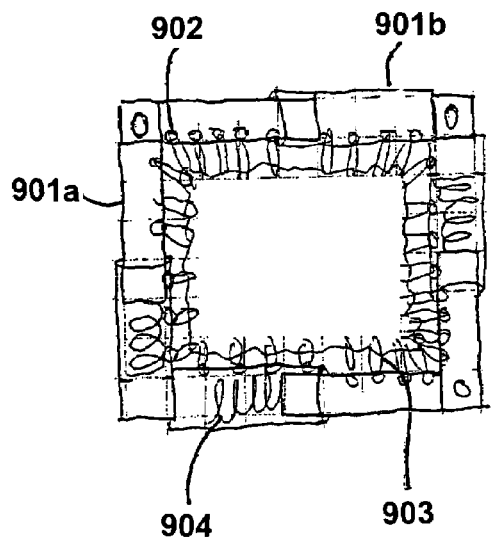
FIG. 9 shows a tissue tensioner that applies tension in two dimensions.

FIG. 9 shows another alternative embodiment of a tissue tensioner. Instead of applying tension in one dimension, on a single axis, this tissue tensioner applies tension in two dimensions. This tissue tensioner is particularly suitable for implants that are in sheet form, for example pericardium and dermis. This tissue tensioner comprises a box configuration so that there is tension in two directions (or along two axes). The tensioner comprises four two-part shafts (each shaft is like the tensioner shown in FIG. 8), with one part of the shaft 901a that telescopes into the other part 901b and engages the spring 904. Holes 902 or some kind of hook could be attached so that sutures 903 could hold the tissue to the tensioner. Again, the tensioner would be compressed (the tension is created) before the implant is fully attached to the tissue tensioner. When the tensioner is released by the operator, it provides tension to an implant sheet in a way similar to a trampoline.

As illustrated by the foregoing descriptions, the fastener can be in the form of blocks, clips, loops, brackets, ratchets, and combinations thereof. The fastener can be a one-piece fastener (for example, as shown in FIG. 5) or a multi-piece fastener (for example, as shown in FIG. 4).

Based on the foregoing embodiments, it is contemplated that suitable tissue tensioners could be built to extend to axial plus radial tensioning or any two or three dimensional tensioning concept.

EXAMPLES

The following examples demonstrate the ability of the present processes and apparatus to reduce damage to implants comprising soft tissue from the treatment of those implants with a cleaning agent such as hydrogen peroxide. The examples contemplate that soft tissues (for example, tendons) can be assessed by observing changes to the collagen within those tendons. Human tendon comprises Type I collagen, the structure of which confers the biological and biomechanical properties of tendons. Aberrations in tendon structure have led to genetic disorders (Ehlers-Danlos syndrome, Osteogenesis imperfecta), acquired disorders (Scurvy), and functional disorders (spontaneous rupture of Achilles tendon) of the tissue. Intact Type I collagen has a unique primary and tertiary structure, by virtue of possessing high levels of glycine and hydroxyproline and is resistant to degradation by most enzymes, except by those from the collagenase family. When the structure of collagen is damaged, it not only results in structural damage, but also altered enzyme lability (chemical damage). Therefore an assessment of tendons at the molecular level by biochemical means can be used as a method to assess tendon integrity or damage. More specifically, assessment of tendons at the molecular level before and after exposure to various chemicals involved in a passivation process can be an effective method of identifying effects of those chemicals on implants.

Trypsin is a serine protease enzyme that is able to digest only those tendons that possess breaks in the intact collagen strands (such as the breaks that occur in denaturation). Therefore, tendon samples can be treated with trypsin, and the level of digestion will indicate the degree of breakage of collagen in these samples. In such a process, digested and undigested (native collagen strands) fractions can be separated, and hydrolyzed with strong acid (for example, using 6N HCl) to release free amino acids from each fraction. Following neutralization of the acid (for example, using 1N NaOH), the levels of hydroxyproline (an amino acid present in high concentrations only in collagen) are assessed in each fraction by a calorimetric method (such as, for example, Chloramine T binding, and reduction of the substrate DAB to a colored end product). The level of denatured collagen in a given sample can then be expressed as a percent of the trypsin-soluble fraction to the sum of the trypsin-soluble and trypsin-insoluble fractions.

In the following examples, a control (unprocessed) tendon was included, often from the same donors used in the example, to compare the effect of the various treatments. Additionally, assay results were standardized based on the weight of the tendons analyzed.

Example 1

Evaluation of Cleaning Agents

Tendon samples (a soft tissue) were exposed to a series of chemicals alone or in combination in order to determine whether collagen damage resulted from the chemicals. These chemicals are cleaning agents used in conventional treatment processes. The effect of these chemicals on collagen structure is shown in Table 1, with a higher number indicating more denatured collagen. Numbers higher than the control are believed to be indicative of collagen damage attributable to the chemicals tested.

TABLE 1

| | | | Percent Average (±St. Dev.) Denatured Collagen Levels (n = 8 for each regime) | | | | | | | |
|---|---|---|---|---|---|---|---|---|---|---|
| | Cont. | Perox. & det (loaded) | Perox. & det (unloaded) | Perox. & SDS | Water | SDS & Triton | Triton | SDS | Perox. | IPOH (@42° C.) |
| Denatured Collagen Levels | 8.006 +/− 0.81 | 15.821 +/− 2.63 | 24.034 +/− 4.93 | 18.908 +/− 0.88 | 10.44 +/− 1.51 | 13.224 +/− 0.14 | 10.889 +/− 1.68 | 11.507 +/− 2.39 | 20.477 +/− 0.17 | 9.065 +/− 0.35 |

These results show that exposure of the tendon samples to hydrogen peroxide alone, or in combination with other chemicals, resulted in an increase in the amounts of denatured collagen in the tendon samples (in other words, resulted in collagen damage to the tendon). Moreover, this also indicated that the other processing chemicals (SDS, Triton, alcohol) did not elicit a similar response in the tendons. The reference in Table 1 to "loaded" refers to tension being applied to the tendon during the period of the tendon's exposure to the chemicals. These results indicate that applying tension to a tendon can reduce the collagen damage from the chemicals. A subsequent experiment, involving tissue from three donors exposed serially to these processing chemicals, tended to confirm the observation.

Example 2

Peroxide Exposure Time

Exposure to peroxide is an effective sterilization method. However, as the time of peroxide exposure increases, the risk of tendon damage also increases. There is generally a degradation time, beyond which there is measurable degradation of the tissue (including collagen), and below which there is no measurable degradation. Tendon samples from three independent donors were exposed to hydrogen peroxide and analyzed for collagen integrity biochemically (as described above). The results are expressed as a ratio of denatured collagen levels present before and after treatment in matched donors. Expressing data in this manner allows one to generalize the effect of chemicals from multiple donors and multiple experiments. A sample representation of the results obtained is shown in Table 2.

TABLE 2

|  | Control | Treated |
|---|---|---|
| Actual Denatured Collagen Levels | 10.02 +/− 1.62 | 16.5 +/− 3.54 |
| Ratio (Treated/Control) | 1.00 | 1.67 +/− 0.42 |

This example confirmed the observation from Example 1 that peroxide exposure results in increased collagen damage. Additional experiments were performed with the same donors, and at two different exposure times. The higher exposure time was twice the lower exposure time. Results (expressed as ratios) are shown in Table 3.

TABLE 3

|  | Control | Treated |
|---|---|---|
| Lower peroxide exposure time | 1.00 | 1.07 +/− 0.14 |
| Higher peroxide exposure time | 1.00 | 1.70 +/− 0.24 |

These results confirm the tendon samples exposed to higher peroxide exposure times experience collagen damage. It was also observed that this effect was irrespective of exposure temperature. These results also suggest that by decreasing the exposure time, collagen damage could be reduced. More importantly, these examples indicate the desirability of contacting a soft tissue with a peroxide for an exposure time sufficient to achieve passivation, but which does not cause excessive collagen damage to tendons. Preferably, a soft tissue is contacted with an oxidizing sterilant such as hydrogen peroxide for less than about 80 consecutive minutes, alternatively no more than about 60 consecutive minutes, alternatively no more than about 40 consecutive minutes, alternatively no more than about 20 consecutive minutes, alternatively no more than about 10 consecutive minutes, alternatively no more than about 5 minutes, alternatively no more than about 60 consecutive seconds, alternatively no more than about 45 consecutive seconds, alternatively no more than about 30 consecutive seconds, alternatively no more than about 20 consecutive seconds, alternatively no more than about 15 consecutive seconds, alternatively no more than about 10 consecutive seconds, alternatively no more than about 5 consecutive seconds, alternatively no more than about 2 consecutive seconds.

Example 4

Alternating Alcohol and Peroxide Exposure

This example evaluates the effect of partitioning the time of peroxide contact with alcohol contact, to test the hypothesis that intermittent or partitioned peroxide contact for a duration may be less damaging to collagen, as compared to a continuous peroxide contact. While the inventors are not to be limited to their theories, another hypothesis is that the intermediate alcohol washes provide a protective effect by transiently fixing the tissue, thereby shielding the tissue matrix from peroxide degradation.

Soft tissue samples were exposed to peroxide either for a continuous treatment or for a partitioned treatment, in which peroxide exposure was partitioned by alcohol washes. In both the continuous treatment and the partitioned treatment, the cumulative time of peroxide exposure was the same. Additionally, two different cumulative times of exposure were evaluated, one that was higher than the degradation time and one that was lower than the degradation time. Collagen levels were compared for all the samples.

For samples tested at the lower cumulative time of peroxide exposure, the collagen damage after continuous and partitioned treatments did not differ in a statistically significant way, though the collagen damage for the continuous period was slightly lower. However, for the samples tested at the higher cumulative time of peroxide exposure, the samples from the partitioned treatment showed significantly less collagen damage than samples from the continuous treatment, indicating the partitioned treatment did not significantly damage the collagen, even though the cumulative time of peroxide exposure was the same as in the continuous treatment. The lower contact time, however, was found to have a reduced sporicidal effect, and thus a reduced passivating effect on the tissue.

This example showed that alternating contact with alcohol and peroxide conferred protection to collagen in samples otherwise exposed for equivalent times to peroxide. This protection allowed effective passivation of the implants comprising soft tissue without excessive damage to the soft tissue.

Example 5

Passivation Of Samples Under Tension

This example assesses the passivating effect of partitioned treatment and the reduction in collagen damage to tensioned tissues. This example also assesses the effects of applying tension to the samples during the partitioned treatment. Tendon samples from 3 different donors were provided. Samples to be evaluated for the passivating effect of the process were spiked with spores of Bacillus stearothermophilus. All the samples were exposed to peroxide for 60 cumulative minutes. Before the first peroxide exposure, and after each period of 20 consecutive minutes of peroxide exposure, the samples were contacted with an isopropanol solution.

In the samples tested for collagen damage, the tensioned samples had significantly less collagen degradation than the unrestrained samples. Moreover, in the samples tested for passivating effect, the period of 60 cumulative minutes of peroxide exposure was sufficient to achieve sufficient passivation.

Example 6

Treatment Process

In this example, the following treatment process is used to passivate an implant comprising soft tissue, more particularly, a tendon graft comprising bone blocks at its ends. The process passivates both the tendon and the bone blocks.

The implant is loaded onto a tissue tensioner similar to that shown in FIG. 5. Tension is applied to the tendon, and the bottom fastener is locked into a tensioning position. The tensioned implant is then placed into a suitable treatment chamber for passivation by a sequence of several cleaning agents contacted with the implant under cyclically increased and decreased pressures. The cleaning agents are provided as aqueous solutions.

After the implant is placed in the treatment chamber, the chamber is filled with an aqueous detergent solution to a level sufficient to immerse the implant in the solution (though with this cleaning agent and those that follow, some head space can remain in the chamber to facilitate rapid pressure cycling). The detergent solution comprises Triton X-100 or another commercially available detergent that has conventionally been used for treating bone and soft tissues, at concentration of about 6.67% (although other concentrations, for example from about 5% to about 8%, may also be used). The pressure in the chamber is then cyclically increased and decreased at a temperature of about 48° C. (although other temperatures, for example from about 40° C. to about 52° C., may also be used). The increased pressure is about 50 PSI above ambient, although other pressures, for example 25 PSI or 75 PSI may be used, and increased pressures will generally range from about 5 PSI above ambient to about 150 PSI above ambient. The increased pressure is maintained for about 10 seconds (alternatively for a time in the range of from about 1 second to about 20 seconds). Then, a decreased pressure is applied for about 110 seconds (alternatively for a time in the range of from about 30 seconds to about 5 minutes), the decreased pressure being about 12 PSI below ambient pressure (alternatively at a pressure in the range of ambient pressure to about 14 PSI below ambient pressure). After ten (or more or fewer) cycles of increased/decreased pressure with the detergent solution, the detergent solution is removed from the chamber.

After the detergent solution, the implant is immersed in an aqueous solution of isopropanol at a concentration of about 85% (though other suitable concentrations, such as from about 70% to about 100% may also be used). While the isopropanol solution contacts the implant, the chamber is then subjected to rapidly cycling pressures to facilitate perfusion of the isopropanol solution into the implant. The pressure in the chamber is cyclically increased and decreased at a temperature of about 42° C. (alternatively, a temperature in the range of from about 40° C. to 48° C.). The increased pressure is about 50 PSI above ambient, although other pressures, for example 25 PSI or 75 PSI may be used, and increased pressures will generally range from about 5 PSI above ambient to about 150 PSI above ambient. The increased pressure is maintained for about 10 seconds (alternatively for a time in the range of from about 5 seconds to about 20 seconds). Then, a decreased pressure is applied for about 50 seconds (alternatively for a time in the range of from about 20 seconds to about 220 seconds), the decreased pressure being about 12 PSI below ambient pressure (alternatively at a pressure in the range of ambient pressure to about 14 PSI below ambient pressure). After ten (or more or fewer) cycles of increased/decreased pressure, the isopropanol solution is removed from the chamber.

After the isopropanol solution, the implant is immersed in an aqueous solution containing a mixture of hydrogen peroxide, at a concentration about 6.67% (although concentrations in the range of about 1% to about 10% may be employed), and Triton X-100, at a concentration of about 6.5% (again, concentrations in the range of about 1% to about 10% may be employed). The pressure in the chamber is cyclically increased and decreased at a temperature of about 48° C. (alternatively, a temperature in the range of from about 40° C. to about 52° C.). The increased pressure is about 50 PSI above ambient, although other pressures, for example 25 PSI or 75 PSI may be used, and increased pressures will generally range from about 5 PSI above ambient to about 150 PSI above ambient. The increased pressure is maintained for about 10 seconds (alternatively for a time in the range of from about 1 second to about 20 seconds). Then, a decreased pressure is applied for about 110 seconds (alternatively for a time in the range of from about 30 seconds to about 5 minutes), the decreased pressure being about 12 PSI below ambient pressure (alternatively at a pressure in the range of ambient pressure to about 14 PSI below ambient pressure). After ten (or more or fewer) cycles of increased/decreased pressure, the peroxide/detergent solution is removed from the chamber.

After the peroxide/detergent solution, the implant is rinsed with water, at a temperature of 48° C. (alternatively, a temperature in the range of from about 40° C. to about 52° C.), in seven cycles of increasing/decreasing pressure. The increased pressure is about 50 PSI above ambient, although other pressures, for example 25 PSI or 75 PSI may be used, and increased pressures will generally range from about 5 PSI above ambient to about 150 PSI above ambient. The increased pressure is maintained for about 10 seconds (alternatively for a time in the range of from about 5 second to about 20 seconds). Then, a decreased pressure is applied for about 20 seconds (alternatively for a time in the range of from about 10 seconds to about 110 seconds), the decreased pressure being about 12 PSI below ambient pressure (alternatively at a pressure in the range of ambient pressure to about 14 PSI below ambient pressure). After the last cycle, the water is removed from the treatment chamber.

Then the implant is contacted with an aqueous solution of isopropanol, as described in detail above.

Next, the implant is immersed in an aqueous solution of hydrogen peroxide at a concentration of about 6.67% (although concentrations in the range of about 1% to about 10% can also be used). The pressure in the chamber is cyclically increased and decreased at a temperature of about 48° C. (or another temperature, for example, in the range of from about 40° C. to about 52° C.). The increased pressure is about 50 PSI above ambient, although other pressures, for example 25 PSI or 75 PSI may be used, and increased pressures will generally range from about 5 PSI above ambient to about 150 PSI above ambient. The increased pressure is maintained for about 10 seconds (alternatively for a time in the range of from about 5 seconds to about 20 seconds). Then, a decreased pressure is applied for about 50 seconds (alternatively for a time in the range of from about 20 seconds to about 220 seconds), the decreased pressure being about 12 PSI below ambient pressure (alternatively at a pressure in the range of ambient pressure to about 14 PSI below ambient pressure). After twenty (or more or fewer) cycles of increased/decreased pressure with the peroxide solution, the peroxide solution is removed from the chamber.

The implant is then rinsed with water through seven (or more or fewer) cycles of increased/decreased pressures, as described in detail above.

Next, the implant is immersed in an alcohol solution having a concentration of isopropanol of from about 50% (though other suitable concentrations, such as from about 30% to about 70%, may also be used). While the isopropanol solution contacts the implant, the chamber is then subjected to rapidly cycling pressures to facilitate perfusion of the isopropanol solution into the implant. The pressure in the chamber is cyclically increased and decreased at a temperature of about 42° C. (alternatively a temperature in the range of from about 40° C. to 48° C.). The increased pressure is about 50 PSI above ambient, although other pressures, for example 25 PSI or 75 PSI may be used, and increased pressures will generally range from about 5 PSI above ambient to about 150 PSI above ambient. The increased pressure is maintained for about 10 seconds (alternatively for a time in the range of from about 5 seconds to about 20 seconds). Then, a decreased pressure is applied for about 50 seconds (alternatively for a time in the range of from about 20 seconds to about 220 seconds), the decreased pressure being about 12 PSI below ambient pressure (alternatively at a pressure in the range of ambient pressure to about 14 PSI below ambient pressure). After ten (or more or fewer) cycles of increased and decreased pressure with the detergent solution, the isopropanol solution is removed from the chamber.

Next, the implant is immersed and contacted again with a peroxide solution for twenty (or more or fewer) cycles at cyclically increased and decreased pressures, as described in detail above.

The implant is then rinsed with water in seven (or more or fewer) cycles of increased and decreased pressures, as described in detail above.

Next, the implant is contacted again with an aqueous solution having an isopropanol concentration of 50% (though other suitable concentrations, such as from about 70% to about 100% may also be used), as described in detail above.

The implant is then rinsed with water, at a temperature of 48° C. (although other temperatures, for example from about 40° C. to about 52° C., may also be used) in seven cycles (or more or fewer), as described above. The water is then withdrawn from the chamber, and more water is added so that the rinse can be repeated. Five rinses are performed to rinse the implant and remove the cleaning agents (although a greater or lesser number of rinses may be performed). Each rinse can include the same or a different number of cycles of increased/decreased pressure; for example each rinse can include seven pressure cycles.

The passivated implant can then be removed from the chamber. The implant may be subject to further steps such as packaging and post-packaging sterilization.

Implants treated according to this procedure do not suffer from excessive or unacceptable collagen damage to the tendons, yet the process is sufficient passivating to provide an implant suitable for implantation into a human or animal recipient. This example suggests that both passivating and collagen sparing effects may be achieved by the present processes and apparatus.

Example 7

Biomechanical Evaluation

This example determined the mechanical changes associated with the processing of preshaped bone tendon bone (BTBs) specimens by contacting with peroxide. Fifteen preshaped BTBs were processed in two runs according to the process in Example 6 and subjected to intermittent peroxide exposure, which was preceded and followed by contact with isopropyl alcohol. Prior to processing, the specimens were mounted to tissue tensioners (of the type shown in FIG. 5) and subjected to 5 Newtons of tension. For most of the tendon specimens, dimensional measurements were recorded after mounting to the tensioner prior to processing and recorded again after processing. The specimens were removed from the tensioner, and frozen to −80° C. to preserve them for later mechanical testing. Care was taken to place the specimens lengthwise and unfolded in a sealable package prior to freezing. Furthermore no kneading, massaging or other manipulation was performed on the specimens.

Dynamic elongation was performed using the Instron Model 5865 Universal Materials Testing Machine. Specimens were subjected to 20 Newtons for 25 minutes while under displacement control. However, the actuator moved under load control to 20 Newtons at time 0 minutes, 5 minutes and 15 minutes. Immediately after the 20 Newtons load was achieved, the actuator switched back to displacement control. Immediately after the pretension step, the tendon was subjected to cyclic loading using the Instron testing machine. For ten of the specimens, data was collected during the pretensioning step in order to assess the amount of elongation that occurred during static pretensioning. Stiffness was determined as the slope of the load displacement curve on the 10th cycle. After 1000 cycles, eight specimens were loaded to failure. Two specimens were subjected to extended cyclic loading for 30,000 and 85,000 cycles respectively.

The highest observed dynamic elongation in this series of specimens was 1.07 mm. Neither of the two specimens that were subjected to extended cyclic loading failed under fatigue. The total elongation of those two specimens was 2.06 mm and 0.90 mm after 30,000 and 85,000 cycles respectively. The elongation that occurs in the pretensioning step was identified to be 0.76±0.21mm (n=10). This data compares favorably with previous data that has been collected on the structural attributes of preshaped BTBs processed by traditional methods.

TABLE 5

Results of Mechanical testing for tendon specimens

| Specimen Number | % Change Gage Length | Dynamic Elongation (mm) | Stiffness (N/mm) | Load at failure (N) |
| --- | --- | --- | --- | --- |
| Average | 1.49% | 0.71 | 184 | 1035 |
| Sd. Dev. | 1.06% | 0.18 | 22 | 202 |
| Count | 11 | 15 | 15 | 8 |

Example 8

Residual Germicides

Residual germicide levels, specifically hydrogen peroxide, were assessed in tendon samples processed according to a process outlined in Example 6. The samples were tensioned during contact with hydrogen peroxide.

Tendons from 4 donors were weighed either as whole BTBs, or divided into bone blocks at mid-substance, and weighed. Samples were then treated according to extract chemicals from the tissue specimens for testing purposes. Eluents were then subjected to peroxide analysis, initially by spectrophotometry, and conventional potassium permanganate titration, according to our validated test protocol. On an average, eluents possessed between 0.02-0.003% peroxide, levels which are neither cytotoxic nor capable of interfering with the normal physiological remodelling process. Further, as mentioned earlier, under these conditions, substantially complete passivation was observed.

Example 9

Histological Analysis

Histological analysis was performed on tendon samples from three donors that were subjected to one of the present processes. Donor tissue was obtained after the intact BTBs underwent successful biomechanical testing. For this analysis, mid-substance (tendinous portion) from each of the three donors were excised from bone blocks, fixed in formalin, embedded, and stained with hematoxylin-eosin. Representative longitudinal and cross-sectional samples were sectioned from these blocks, and viewed under light microscope. Features that were specifically examined in these sections include, efficiency of the present process to decellularize the tendon, and preserve collagen architecture.

Example 10

Implantation of Bone-Tendon-Bone Grafts in Animal Recipients

In this example, bone-tendon-bone grafts (BTBs) produced by an embodiment of the present processes and implanted into sheep were assessed. Bone-tendon-bone grafts comprising patellar tendon and associated bone blocks were obtained from donor sheep and treated according to the process disclosed in Example 6 to provide passivated implants. These implants were used to reconstruct the knees of six sheep following resection of their native anterior cruciate ligament (ACL).

The study lasted for 24 weeks. During the study, the implants were assessed by both non-invasive (gait analysis and knee laxity measurements) and invasive (histological, pathological and destructive mechanical tests following euthanasia) methods at various time points. Knee laxity was assessed as anterior-posterior laxity at defined loads (15, 20 and 30 lbs) using an arthrometer at 6, 10, 12, 18, and 24 weeks after surgery. As control measurements, laxity measurements were also obtained prior to surgery, and soon after ACL resection. Pathological observation of the implants were recorded at the following times when select animals were euthanized: two implants at 6 weeks, two implants at 12 weeks, and six implants at 24 weeks). The pathological observation included observations of the entire operated knee, as well as synovial fluid and draining lymph nodes. Detailed histological observations of the graft (femoral and tibial insertion sites, midsubstance) and draining lymph nodes were performed.

The gait analysis indicated no appreciable difference in the gaits of sheep that received the implants described above, as compared treated according to standard methods. The knee laxity measurements and destructive mechanical tests indicated that the implants did not have excessive laxity or weakness. The histological and pathological test results indicated positive remodeling features indicating new bone growth, progressing to successful incorporation of the graft at both bone tunnels and mid-substance. In particular, analysis of the synovial fluid for levels of cells, glucose and enzymes showed differences in comparison to un-operated control knees, with changes indicative of an actively remodeling site (non-infectious arthropathy). These analyses and results demonstrate that the present processes may be used to passivate an implant comprising a soft tissue without causing excessive damage to the soft tissue.

All patents, test procedures, and other documents cited herein, including priority documents, are fully incorporated by reference to the extent such disclosure is not inconsistent with this invention and for all jurisdictions in which such incorporation is permitted.

While the present invention has been described and illustrated by reference to particular embodiments, it will be appreciated by those of ordinary skill in the art that the invention lends itself to many different variations not illustrated herein. For these reasons, then, reference should be made solely to the appended claims for purposes of determining the true scope of the present invention.

Although the appendant claims have single appendencies in accordance with U.S. patent practice, each of the features in any of the appendant claims can be combined with each of the features of other appendant claims or the main claim.

What is claimed is:

1. A process for making an implant more suitable for implantation into a recipient, wherein the implant at least partially comprises a soft tissue, the process comprising:
   (a) contacting the implant with a protective agent selected from the group consisting of alcohols and polyols;
   (b) contacting the implant with an oxidizing sterilant; and
   (c) contacting the implant with a rinsing fluid, further comprising applying tension to the soft tissue at least during part of step (b).

2. The process of claim 1, wherein at least one of steps (a), (b) or (c) further comprises cyclically increasing and decreasing pressure during the contact with the implant.

3. The process of claim 1, further comprising:
   (d) contacting the implant with an oxidizing sterilant; and
   (e) contacting the implant with a rinsing fluid.

4. The process of claim 3, wherein at least one of steps (a) through (e) further comprises cyclically increasing and decreasing pressure during the contact with the implant.

5. The process of claim 1, further comprising the step of rinsing the implant with an aqueous solution between steps (b) and (c).

6. The process of claim 1 wherein prior to step (b), the implant contains an amount of the alcohol in the soft tissue sufficient to reduce damage from oxidation to the soft tissue.

7. The process of claim 1, wherein the rinsing fluid is selected from the group consisting of alcohols, polyols, acetone, water, and mixtures thereof.

8. The process of claim 1, wherein the rinsing fluid comprises a monohydric alcohol having one to eight carbon atoms.

9. The process of claim 1, wherein step (b) comprises contacting the implant with an aqueous solution comprising hydrogen peroxide in a concentration range of from about 1% to about 10%.

10. The process of claim 1, wherein the implant comprises at least one tendon or ligament.

11. The process of claim 1, wherein the implant comprises a tendon having bone attached thereto.

12. A process for making an implant more suitable for implantation into a recipient, wherein the implant at least partially comprises a soft tissue, the process comprising:
   (a) contacting the implant with a protective agent selected from the group consisting of alcohols and polyols;
   (b) contacting the implant with an oxidizing sterilant; and
   (c) contacting the implant with a rinsing fluid,
   further comprising: applying kinematic restraint to the soft tissue during each of steps (a), (b) and (c).

13. The process of claim 12, wherein at least one of steps (a), (b) or (c) further comprises cyclically increasing and decreasing pressure during the contact with the implant.

14. The process of claim 12, further comprising:
   (d) contacting the implant with an oxidizing sterilant; and
   (e) contacting the implant with a rinsing fluid.

15. The process of claim 14, wherein at least one of steps (a) through (e) further comprises cyclically increasing and decreasing pressure during the contact with the implant.

16. The process of claim 12, further comprising the step of rinsing the implant with an aqueous solution between steps (b) and (c).

17. The process of claim 12 wherein prior to step (b), the implant contains an amount of the alcohol in the soft tissue sufficient to reduce damage from oxidation to the soft tissue.

18. The process of claim 12, wherein the rinsing fluid is selected from the group consisting of alcohols, polyols, acetone, water, and mixtures thereof.

19. The process of claim 12, wherein the rinsing fluid comprises a monohydric alcohol having one to eight carbon atoms.

20. The process of claim 12, wherein step (b) comprises contacting the implant with an aqueous solution comprising hydrogen peroxide in a concentration range of from about 1% to about 10%.

21. The process of claim 12, wherein the implant comprises at least one tendon or ligament.

22. The process of claim 12, wherein the implant comprises a tendon having bone attached thereto.

23. A process for treating an implant so as to sterilize the implant prior to implantation, the implant comprising a soft tissue, the process comprising:
applying tension to the soft tissue while contacting the soft tissue with a cleaning agent.

24. The process of claim 23 wherein from about 0.5 Newton to about 20 Newtons of tension are applied to the soft tissue.

25. The process of claim 23 wherein from about 1 Newton to about 10 Newtons of tension are applied to the soft tissue.

26. The process of claim 23 wherein from about 3 Newtons to about 5 Newtons of tension are applied to the soft tissue.

27. The process of claim 23 wherein the cleaning agent comprises an oxidizing sterilant.

28. The process of claim 27 wherein the oxidizing sterilant is a peroxide.

29. The process of claim 28, wherein the peroxide is an aqueous solution of hydrogen peroxide.

30. The process of claim 23 wherein the cleaning agent comprises a disinfectant.

31. The process of claim 23 wherein the cleaning agent is a decontaminating agent.

32. The process of claim 23 wherein the cleaning agent comprises a detergent.

33. The process of claim 23 wherein the cleaning agent is selected from the group consisting of alcohols, polyols, detergents, and mixtures and combinations thereof.

34. The process of claim 23 further comprising the step of contacting the implant with an alcohol before contact with the cleaning agent.

35. The process of claim 23, further comprising the step of contacting the implant with a rinsing fluid after contact with the cleaning agent.

36. The process according to any of claims 23, 30, 31, 32, or 33, further comprising the step of cyclically increasing and decreasing pressure while the cleaning agent contacts the implant.

37. The process of claim 23 wherein the implant comprises at least one tendon or ligament.

38. The process of claims 23 wherein the implant comprises a tendon having bone attached thereto.

39. A process for making an implant more suitable for implantation into a recipient, wherein the implant at least partially comprises a soft tissue, the process comprising:
(a) contacting the implant with an alcohol;
(b) contacting the implant with a peroxide for less than about 80 minutes;
(c) contacting the implant with an alcohol; and
(d) applying tension to the implant during at least one of steps (a), (b) or (c).

40. A process for making an implant more suitable for implantation into a recipient, wherein the implant at least partially comprises a soft tissue, the process comprising:
applying tension to the implant;
perfusing the tensioned implant with an alcohol; and
perfusing the tensioned implant with a peroxide for less than about 80 cumulative minutes.

\* \* \* \* \*

UNITED STATES PATENT AND TRADEMARK OFFICE
CERTIFICATE OF CORRECTION

| | |
|---|---|
| PATENT NO. | : 7,648,676 B2 |
| APPLICATION NO. | : 10/828653 |
| DATED | : January 19, 2010 |
| INVENTOR(S) | : Mills et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 677 days.

Signed and Sealed this

Twenty-third Day of November, 2010

David J. Kappos
*Director of the United States Patent and Trademark Office*